(12) United States Patent
Pellican et al.

(10) Patent No.: US 7,996,239 B1
(45) Date of Patent: Aug. 9, 2011

(54) SYSTEM AND METHOD FOR GENERATING A DISPLAY TO GRAPHICALLY INDICATE STATE FOR A SERIES OF EVENTS

(75) Inventors: Suzanne Pellican, Menlo Park, CA (US); Robert Pellican, Menlo Park, CA (US)

(73) Assignee: Intuit Inc., Mountain View, CT (US)

( * ) Notice: Subject to any disclaimer, the term of this patent is extended or adjusted under 35 U.S.C. 154(b) by 1018 days.

(21) Appl. No.: 11/829,652

(22) Filed: Jul. 27, 2007

(51) Int. Cl.
*G06Q 50/00* (2006.01)
*G06Q 10/00* (2006.01)

(52) U.S. Cl. .................................. 705/2; 705/3
(58) Field of Classification Search ........... 705/2
See application file for complete search history.

(56) References Cited

U.S. PATENT DOCUMENTS

| | | | |
|---|---|---|---|
| 5,182,705 A | 1/1993 | Barr | |
| 5,630,069 A | 5/1997 | Flores | |
| 6,859,783 B2 | 2/2005 | Cogger | |
| 2005/0203828 A1* | 9/2005 | Lyakovetsky | 705/38 |

OTHER PUBLICATIONS

Belluci, Integrating artificial intelligence, argumentation and game theory to develop an online dispute resolution environment, Tools with Artificial Intelligence, 2004. ICTAI 2004. 16th IEEE International Conference on.*

* cited by examiner

*Primary Examiner* — Luke Gilligan
*Assistant Examiner* — Tran Nguyen
(74) *Attorney, Agent, or Firm* — Gunnison, McKay & Hodgson, L.L.P.; Philip McKay

(57) ABSTRACT

Various embodiments of a system and method for generating a display configured to graphically indicate a state of a series of events are described. The system and method may include a display generator configured to generate display data that defines a display configured to indicate the state of a series of events. The display generator may create display data that defines a display configured to graphically indicate such events in a chronological manner such that the user may easily view the current state of the particular process. The display data may define a display that graphically indicates multiple events from multiple entities, such as events associated with a same episode. The displays defined by the display data may include one or more visual elements that graphically indicate an event that includes the transfer of an asset between a source entity and a destination entity.

31 Claims, 19 Drawing Sheets

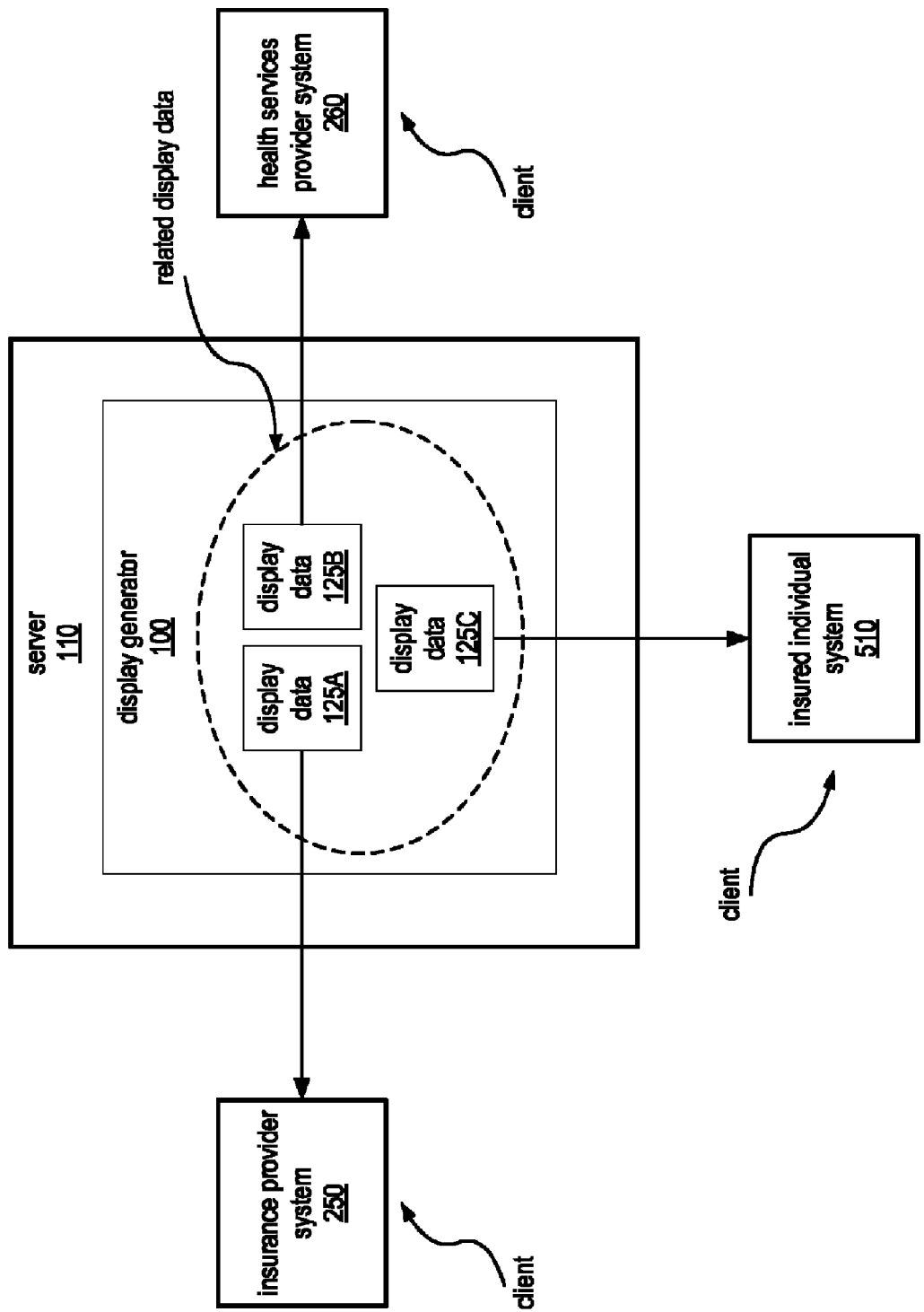

SYSTEM AND METHOD FOR GENERATING A DISPLAY TO GRAPHICALLY INDICATE STATE FOR A SERIES OF EVENTS

BACKGROUND

Many individuals and families utilize health insurance plans to pay for medical expenses. For example, when an individual visits a physician's office for a medical checkup, the individual may pay for health services with personal funds (e.g., a copayment) and funds provided by a health insurance plan. Typically, to utilize health insurance coverage for health services, an appropriate claim must be filed with the insurance company in order to receive benefits.

Successfully processing a medical insurance claim may require the individual, the insurance company, and/or the healthcare provider to exchange a variety of items, such as payments, claim information, information pertaining to services rendered, and other information. Processing of the medical insurance claim may be complete once each party has provided and/or received the necessary items.

Numerous problems may occur during insurance claim processing. For example, the healthcare provider may file the wrong claim with the insurance company, or the insurance company may improperly deny coverage for a medical procedure covered under an individual's health insurance plan. In other cases, a healthcare provider may transmit an incorrect bill to the insurance company and/or insured individual, such as a bill including incorrect service charges or charges for services that were not rendered. Another example of a problem that may occur during insurance claim processing may include an individual (e.g., a patient) failing to remit payment to a healthcare provider or an individual failing to obtain appropriate referrals for particular health services. In many cases, the responsibility for rectifying such problems lies on the insured individual. For example, it may be necessary for the insured individual to contact the insurance company and/or the healthcare provider to determine steps that have been taken to process the claim as well as steps that need to be taken to complete the processing of the claim.

SUMMARY

Various embodiments of a system and method for generating a display to graphically indicate a state of a series of events are described. The system and method for generating a display may include a display generator configured to access information associated with a service or an episode. One or more portions of the information accessed by the display generator may be provided by each of various entities including an insurance provider and a service provider. The display generator may generate display data that defines a display configured to graphically indicate a state of a series of events associated with the service or episode. To graphically indicate the state of the series of events the display may include multiple chronologically ordered visual elements that are associated with a portion of the accessed information. In various embodiments, the visual elements may graphically indicate an asset associated with the health related service as well as a source entity and a destination entity of the multiple entities. In general, the source entity may be an entity that previously provided the asset to the destination entity.

BRIEF DESCRIPTION OF THE DRAWINGS

FIG. 5 is a data flow diagram illustrating an exemplary embodiment of a system configured to generate and manage display data.

Figure 1:
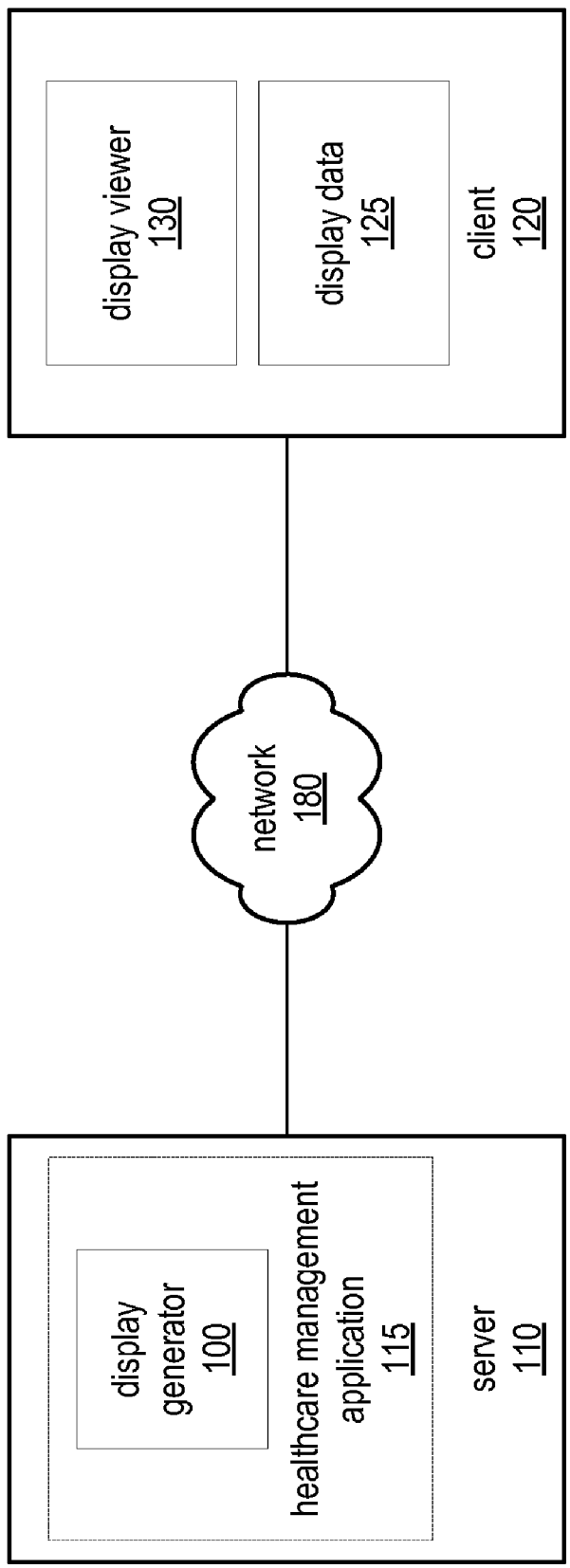
FIG. 1 is a block diagram illustrating an exemplary embodiment of a system configured to generate display data.

While the system and method for generating a display is described herein by way of example for several embodiments and illustrative drawings, those skilled in the art will recognize that the system and method for generating a display is not limited to the embodiments or drawings described. It should be understood, that the drawings and detailed description thereto are not intended to limit embodiments to the particular form disclosed. The intention is to cover all modifications, equivalents and alternatives falling within the spirit and scope of the system and method for generating a display as defined by the appended claims. Any headings used herein are for organizational purposes only and are not meant to limit the scope of the description or the claims. As used herein, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

Various embodiments of a system and method for generating a display configured to graphically indicate a state of a series of events are described. The system and method for generating a display may include a display generator configured to generate display data that defines a display configured to indicate the state of a series of events associated with a service (e.g., a health insurance claim and/or a health service) and/or episode. An episode may include multiple services associated with a common event. For example, one type of episode may include a pregnancy episode that includes multiple health services (e.g., check ups, prescription drug disbursements, and other services) each associated with an individual's pregnancy.

When an individual visits a physician's office for health services (e.g., check-up, blood test, physical examination, and other health related services), various series of events may follow as a result of the rendered health services. One such series of events is a payment process associated with the rendered health service. In some cases, the individual may utilize health insurance to pay for a portion of the amount owed for the health service. For instance, in some cases, the insured individual may pay for a portion of the amount owed, such as a copayment, and the insurance company may provide payment for the remainder of the amount owed after the copayment has been applied. In such a situation, numerous events may occur including, but not limited to, the health services provider sending an insurance claim (on behalf of the insured individual) to the insurance company, the health services provider sending a bill to the insured individual, the insurance company processing the insurance claim, the insurance company sending an Explanation of Benefits (EOB) statement to the insured individual, the insurance company providing a payment to the health services provider, and/or the insured individual providing a payment to the health services provider. Various other events, such as events related to disputes (e.g., disputes related to billing or insurance coverage), may also occur.

The display generator described herein may create display data that defines a display configured to graphically indicate such events in a chronological manner such that the user may easily view the current state of the particular series of events. For example, the display may graphically indicate that a physician or other health services provider is currently awaiting payment for a rendered health service. In various embodiments, the display data may define a display that graphically indicates multiple events from multiple entities (e.g., one or more health services providers, one or more individuals or patients, and one or more insurance companies). For instance, some insured individuals may receive insurance coverage from a primary health insurance plan (e.g., insurance provided by a private entity) and a secondary health insurance plan (e.g., insurance provided by a government entity). In this manner, the display defined by the display data may consolidate the actions of multiple entities into a single view.

In various embodiments, the displays defined by the display data may include one or more visual elements. The visual elements may graphically indicate an event that includes the transfer of an asset (i.e., data, information, payments, and other items related to an insurance claim or health service) between a source entity (i.e., the entity providing the asset) and a destination entity (i.e., the entity receiving the asset). For example, an exemplary event may include an individual (the source entity in this example) providing a health services provider (the destination entity in this example) with a payment (the asset in this example). The displays and/or display data generated by the display generator may include multiple visual elements in order to graphically indicate the current state of a series of events, such as events associated with health services, health episodes, and/or payments for such health services and health episodes. Various examples of displays defined by data generated by the display generator are described herein and illustrated in FIGS. 4A-4M.

An exemplary system in which a display generator may be implemented is illustrated by the block diagram of FIG. 1. A display generator, such as display generator 100, may be implemented within a computer system, such as server 110. Server 110 and client 120 may be coupled via one or more networks, such as network 180. Network 180 may be any of various computer networks including, but not limited to, Local Area Networks (LANs) (e.g., corporate or Ethernet networks), Wide Area Networks (WANs) (e.g., the Internet), wireless networks, telecommunications networks, or a combination thereof. Additionally, server 110 and client 120 may be any of various computer systems or devices including, but not limited to, server computer systems, desktop computer systems, laptop computer systems, Personal Digital Assistants (PDAs), mobile phones, and other devices configured to communicate over a network, such as network 180. In some embodiments, server 110 and client 120 may communicate according to a traditional client-server architecture. In other embodiments, server 110 and client 120 may communicate according to other types of architectures, such as a peer-to-peer architecture. In regard to server 110 and client 120, the terms "server" and "client" generally refer to the relationship of the systems in regard to display data. In other words, architectures other than typical client-server architectures may be employed.

In various embodiments, client 120 may receive display data, such as display data 125, from display generator 100. Display data may include data that enables client 120 to present a display (e.g., through a computer monitor) to a user.

In various embodiments, client 120 may include a display viewer, such as display viewer 130, which enables a user to view one or more displays defined by display data 125. For example, in some embodiments, display viewer 130 may be a web browser or other application configured to display web content, such as Microsoft Internet Explorer™, Netscape Navigator™, Mozilla Firefox™, or any application that is capable of accessing and displaying documents or web pages, such as according to the Hypertext Transport Protocol (HTTP). In such an embodiment, display data 125 may include elements of various markup languages, such as Hypertext Markup Language (HTML) or Extensible Markup Language (XML), and other markup languages.

In various embodiments, the display generator described herein may be configured to interact with a healthcare management application. For example, display generator 100 may be implemented as a component of healthcare management application 115. The healthcare management application may in some embodiments provide a consumer with a framework and tools for collecting, organizing, and managing data related to their health history; past, current and future health services; health insurance plan(s) (e.g., what services are covered, coverage limits, claims status, and explanations of benefits); and finances related to healthcare (e.g., health insurance premiums, deductibles, co-payments, benefit payments, reimbursements from FSAs, HRAs, or health savings accounts, maximum out-of-pocket expenses, and maximum lifetime benefits.) For example, a healthcare management application may be configured to provide a consumer with a comprehensive and detailed health history, or may allow the consumer to extract and/or analyze his or her data regarding a particular health condition or event (e.g., an injury or illness) or a particular healthcare-related service (e.g., a particular diagnostic exam or a course of treatment for a chronic condition.)

A healthcare management application may in some embodiments be implemented as a web-based service to which consumers and/or employers may subscribe. In other embodiments, it may be implemented as a stand-alone application, such as one installed and executed on a desktop computer by a consumer. In some embodiments, a healthcare management application may include both a locally installed application (i.e., a client portion) and a remote, web-based application (i.e., a server portion). For example, in one embodiment, a consumer may enter healthcare-related information on a locally installed client application and then may upload the information to a healthcare management service server for secure storage and/or further analysis.

In various embodiments, the healthcare management application may receive information from one or more of: a consumer, one or more healthcare providers, one or more health plan administrators (e.g., health insurance representatives), and one or more financial institutions. The information received and/or managed by a healthcare management application may be formatted according to a standard data exchange format, in some embodiments.

The healthcare management application may in some embodiments maintain healthcare-related information in one or more databases (or in other suitable formats) in a local or remote memory, or in a combination of the two. For example, a database located on a healthcare management service server may be configured to securely store healthcare-related information for multiple individual consumers or for employees of one or more corporations subscribing to the healthcare management service, while a database stored locally on a consumer's computing system may include only his or her own personal healthcare-related data. The information managed by a healthcare management application may in some embodiments be extracted for use by other applications, such as the display generator described herein. For example, display generator 100 may use application data from application 115 to create display data 125.

In various embodiments, client 120 may be utilized by an insured individual to view one or more displays defined by display data 125. In other cases, server 110 may provide display data to a multiple clients. For example, a customer service representative (CSR) of an insurance company may use a client configured in the same (or similar) manner as client 120 to view one or more displays defined by display data 125. In other words, while a single client is illustrated in FIG. 1, server 110 may serve multiple clients (e.g., computer systems associated with an insured individual, an insurance company, and/or a health services provider) each configured in the manner of client 120.

In some embodiments, the functionality of display generator 100 (as well as healthcare management application 115) may be implemented within client 120 such that the client may generate its own display data and corresponding displays. For example, in some embodiments, health care management application 115 and display generator 100 may be implemented as a standalone application on client 120.

Figure 2:
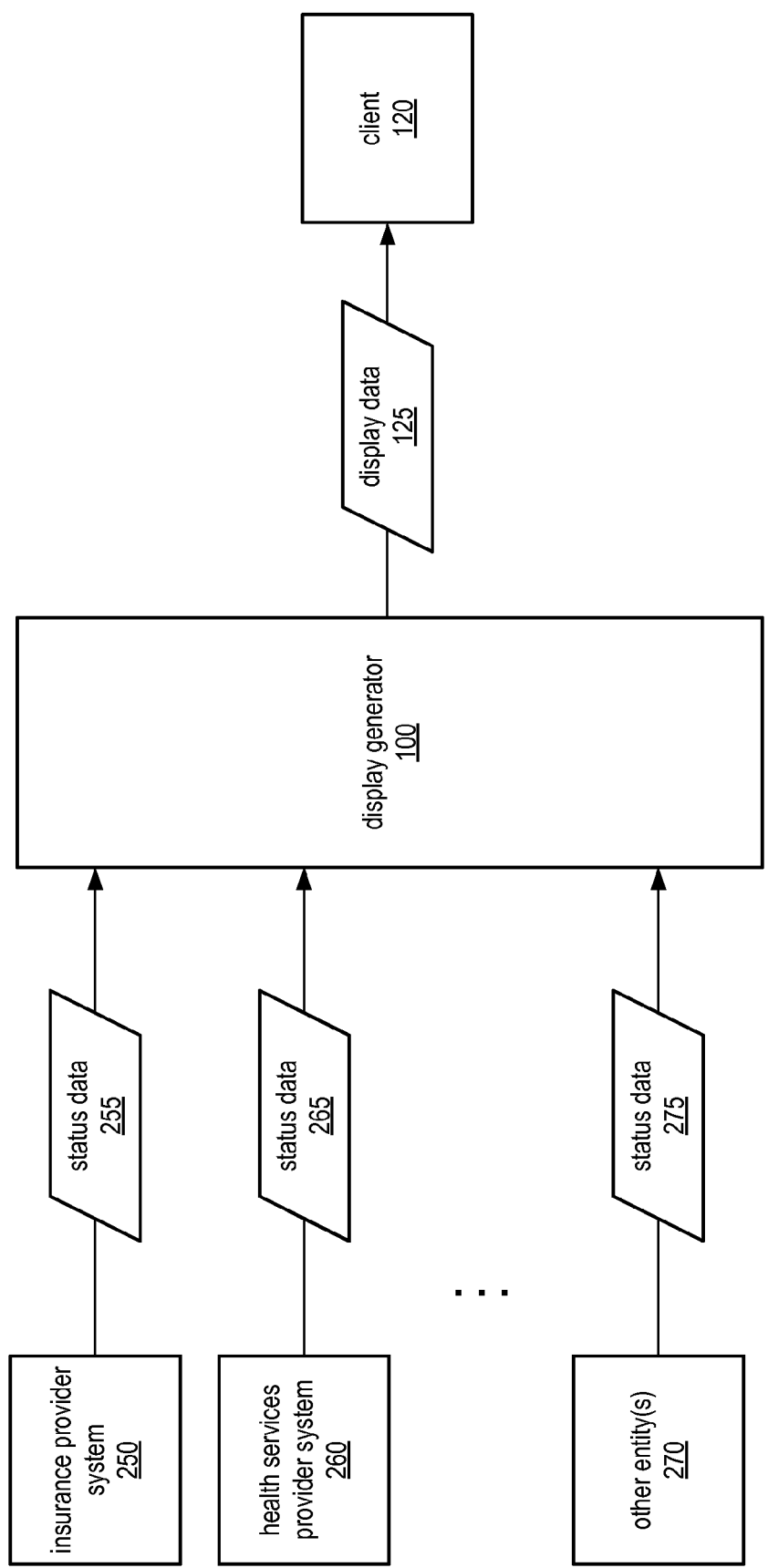
FIG. 2 is a data flow diagram illustrating an exemplary embodiment of a system configured to generate display data.

In various embodiments, display generator 100 may use information and/or data from various entities to create display data, such as display data 125. Such information and/or data may include information pertaining to events associated with a rendered medical service, such as the various events described herein. FIG. 2 illustrates an exemplary data flow diagram of the collection of information and creation of display data. In various embodiments, display generator 100 may receive status data from various entities, such as insurance provider system 250, health services provider system 260, and other entities, such as other entity(s) 270 configured to provide status data pertaining to one or more events. In various embodiments, insurance provider system 250 may represent a computer system associated with a health insurance provider. Insurance company system 250 may provide status data 255 to display generator 100. Status data 255 may include data that indicates an event associated with one or more medical services, one or more insurance claims, and/or one or more insured individuals. For example, a health insurance provider may receive an insurance claim from a health services provider, such as an insurance claim filed on behalf of one of the health services provider's patients. In response, the health insurance provider may provide a payment to the health services provider and/or send an EOB to the patient. Status data 255 may indicate such actions (e.g., the sending of payments, EOBs, and other actions). In this way, display generator 100 may have access to status data that reflects an up-to-date view of an entity's actions. Similarly, health service provider system 260 may provide status data 265 to display generator. Status data 265 may indicate various actions of the health service provider. For instance, status data 265 may indicate that the health services provider has rendered a particular health service to an individual, sent a bill or invoice to an individual, and/or filed an insurance claim with a health insurance provider. Please note, the actions and/or events provided herein in regard to status data are exemplary. Indeed, in various embodiments, status data may indicate other types of events or actions. In some embodiments, additional entities, such as other entity(s) 270 (e.g., additional insurance providers or health services providers) may provide status data, such as status data 275, to display generator 100. In various embodiments, status data may also include data associated with other items including, but not limited to, representations (e.g., text or image) of bills, claims, EOB statements, payments (e.g., check images), call records, chat records, and other items.

Display generator 100 may use the status data to create display data, such as display data 125. In various embodiments, display data 125 may define a display configured to graphically indicate a state of a series of events associated with one or more healthcare related services or insurance claims. For example, display data 125 may define a display associated with a cholesterol check. Such a display may include graphical indications of events such as the filing of claim, the sending of a bill, the sending of an Explanation of Benefits (EOB) statement, the processing of a claim, and various other events, such as the events described herein. For instance, display data 125 may define various displays that assist a user in determining the current state of a series of events associated with a healthcare-related service. One such series of events may include events associated with the processing of an insurance claim for a rendered healthcare-related service. For example, such events may include a health services provider sending (or filing) a claim with an insurance company, a health services provider sending a bill or invoice to an insured individual, an insurance company sending an EOB to an insured individual, an insurance company sending payment to a health services provider, and other events described in more detail below.

Figure 3:
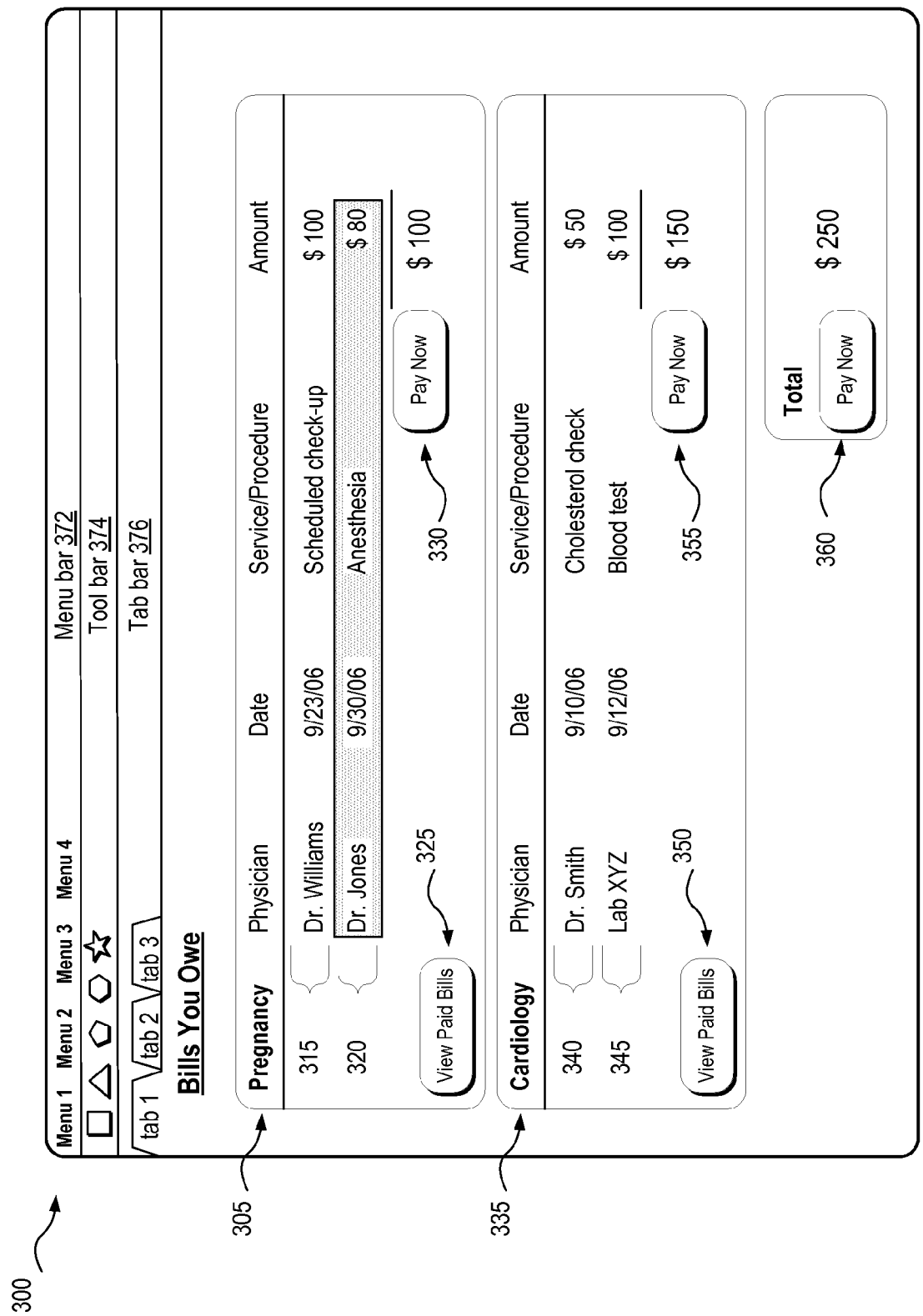
FIG. 3 illustrates an exemplary display that may serve as a launch point for other displays.

Various exemplary displays that may be defined by display data that may be generated by display generator 100 are described below in regard to FIGS. 4A-4M. FIG. 3 illustrates an exemplary display, such as display 300, which may be defined by display data 125. In various embodiments, display 300 may serve as an access point for other displays as described herein. In embodiments, display 300 may be a display of a healthcare management application, such as healthcare management application 115. In some cases, display 300 may be a display of a web browser. For example, a user may be presented with display 300 upon accessing an online healthcare management application. Display 300 may include various toolbars for providing accessing application functionality, such as functionality of a healthcare management application. Menu bar 372 may enable a user to access one or more menus including user-selectable options that correspond to application functions. Similarly, toolbar 374 may include one or more icons or other controls for selecting various application functions. Tab bar 376 may facilitate application navigation. In other words, a user may select one or more tabs of the tab bar in order to view various portions of the application. Various other types of toolbars and/or controls may also be included within the displays described herein.

Display 300 may assist a user with organization of medical bills and/or insurance claims. For instance, display 300 may be a display of a health care management application. In some embodiments, display 300 may be organized according to a health episode. For example, a particular health episode, such as a pregnancy, may include numerous health services, such as scheduled check-ups, anesthesia, and other health services. One such episode is illustrated by episode display portion 305. Display portion 305 illustrates two health service entries (e.g., health service entries 315 and 320) that correspond to health services rendered to an individual (e.g., a check-up and anesthesia). As illustrated by episode display portions 305 and 335, each health service entry may include information associated with a particular health service or procedure including, but not limited to, the name of the physician that rendered the service, the date the service was rendered, as well as the amount billed for the service. In some embodiments, an episode display portion may include a health service entry for future services, such as health service entry 320. In the exemplary display, health service entry 320 is "grayed-out" to indicate that the entry corresponds to a rendered health service for which the user (e.g., an insured individual) has not yet received a bill. While the exemplary display illustrates health service entry 320 as grayed-out, other types of visual indicators (e.g., flags, icons, bolding, highlighting, etc) may be employed to indicate a bill that has not been received. In some embodiments, if the user attempts to pay for a service that is grayed-out (e.g., the individual has not received a bill for the service or claim adjudication for the service is incomplete), the display may present one or more visual warnings (e.g., pop-up displays or dialog boxes) that warn the user about paying for the associated service and, in some cases, suggest that the user refrain from paying the bill temporarily.

In various embodiments, display 300 may enable a user to view bill records, such as through the selection of buttons 325 or 350. For example, button 325 may be selected to view paid bills associated with past pregnancy services or procedures. In various embodiments, display 300 may be integrated with a payment system such that a user may pay bills or invoices for various health services. For instance, the selection of payment buttons 330 and/or 355 may enable a user to pay bills for respective episodes. In some cases, the selection of a payment button may enable a user to pay for multiple bills associated with the same episode at the same time. In other words, instead of requiring the user to pay for each service or procedure individually, the user may pay (e.g., by selecting button 355) for multiple (or all) services or procedures through a single payment process. For instance, if a user selects button 355, display 300 may interface with a payment system such that both the cholesterol check and the blood test of entries 340 and 345 may be paid for through a single payment process. In various embodiments, a single payment process may pay for multiple services rendered by different physicians (or other entities such as laboratories). In some embodiments, a user may pay for health services of multiple episodes simultaneously. For instance, a user may pay for all outstanding bills by selecting payment button 360. In response, display 300 may interface with a payment system such that all outstanding bills for each episode are paid through a single payment process.

Display 300 may serve as an access point or launch point for other displays. In various embodiments, each health services entry (e.g., entries 315, 320, 340 or 345) may be user selectable in order to view additional information (e.g., additional displays) related to the particular health service. In other words, each health service entry may serve as a launch point for additional displays. Such additional displays may be illustrated by the exemplary display(s) of FIGS. 4A-4M. FIGS. 4A-4M illustrate a display, such as display 400, configured to graphically indicate a state of a series of events associated with one or more health services. Such events may include but are not limited to, the health services provider sending an insurance claim (on behalf of the insured individual) to the insurance company, the health services provider sending a bill to the insured individual, the insurance company processing the insurance claim, the insurance company sending an Explanation of Benefits (EOB) statement to the insured individual, the insurance company providing a payment to the health services provider, and/or the insured individual providing a payment to the health services provider. Various other events, such as events related to disputes (e.g., disputes related to billing or insurance coverage), may also be graphically indicated by displays generated by display generator 100. In various embodiments, elements of display 300 and elements of display 400 may be integrated into a single display.

Display 400 may be utilized by one or more users, such as a user of a healthcare management application. Accordingly, display 400 may include one or more user interface elements such as menu bar 452, tool bar 454, and tab bar 456, which may be similar to the corresponding interface elements of FIG. 3. In various embodiments, display 400 may include one or more visual elements. Visual elements may be used to indicate information about an event to a user. In many cases, the visual element may indicate information about an event that includes the transfer of an asset from a source entity to a destination entity. Assets may include any of various items including, but not limited to, insurance claims (including submissions or filings), bill payments, EOBs, and other items or information. Source entities and destination entities may include individuals (e.g., insured individuals or family members of insured individuals), insurance companies (e.g., health insurance companies and other providers of insurance), health service providers (e.g., physicians, laboratories, pharmacies, and other providers of health services). In other words, a visual element may indicate the transfer of an asset from a source entity to a destination entity. For example, a visual element may indicate that a user (the source entity in this example) has provided a payment (the asset in this example) to a physician's office (e.g., the destination entity in this example). In various embodiments, multiple visual elements may be displayed in the same display to illustrate a history or record of events. In embodiments, the visual elements may be chronologically ordered. In various embodiments, other types of events may also be indicated by various display elements including but not limited to, office visits, laboratory visits, and/or pharmacy visits.

In various embodiments, a visual element may be associated with data received by display generator 100. As described above in regard to FIG. 2, display generator 100 may receive data or information (e.g., status data) from various entities, such as health service providers, insurance companies, and other entities. The data received may be used by the display generator to create data that defines one or more visual elements. For example, a health services provider may provide the display generator with information that indicates the health service provider sent a claim (e.g., a health insurance claim filed on behalf of a patient) to an insurance provider. Visual element 410 illustrates such a situation. Visual element 410 includes an indication of an asset (e.g., claim icon 4020) and an indication of the source and destination entities (e.g., arrow 4015). In this example, the tail of arrow 4015 indicates the source entity (e.g., the health service provider), and the head of arrow 4015 indicates the destination entity (e.g., the insurance provider). While visual element 410 includes an arrow and an icon to illustrate a source entity, destination entity, and an asset, various other types of indicators may be utilized in other embodiments. In general, visual elements may include any type of indicator to illustrate a source entity, destination entity, and/or an asset.

Display generator 100 may update the display data (e.g., display data 125) that defines display 400. For example, display generator 100 may update display data in response to receiving new data from one or more entities, such as entities 250-270 described above. For instance, a health services provider system may provide display generator 100 with additional data indicating that a bill has been sent to a patient for health services. In response, display generator 100 may update and/or regenerate display data (e.g., display data 125) such that a display defined by such data is updated to indicate the event. FIG. 4B illustrates another visual element (e.g., visual element 425), which illustrates the health services provider sending a bill to a patient. For instance, after providing one or more health services to an insured individual (e.g., patient), a health services provider bill (or invoice) the individual for the particular service. Similar to the visual element 4010, visual element 425 indicates an asset (e.g., via $1^{st}$ Bill icon 4035), a source entity (e.g., health services provider), and a destination entity (e.g., insurance provider).

In various embodiments, the displays described herein may include one or more action indicators that indicate an action, such as an action the insured individual should perform in response to a particular event. In other words, the display may be configured to indicate an action to be performed in response to the state of events indicated by the display. For example, as illustrated by visual element 4025, a health services provider may send a $1^{st}$ bill to an individual. However, in some cases, it may be necessary for an individual to ignore a $1^{st}$ bill. For instance, it may be standard practice for a health services provider to send a $1^{st}$ bill to an individual irrespective of whether the individual is covered by a health insurance policy. When an individual is uninsured, it may be appropriate for the individual to pay the first bill received from a health services provider. However, when an individual is insured by a health insurance policy, it may be appropriate for the individual to ignore the first bill received from a health services provider. By ignoring the first bill received, the individual may avoid overpayment since in many cases the first bill received may not be adjusted for payments made from the individual's health insurance provider to the health services provider. In some cases, ignoring a bill (as well as various other actions) may not be readily apparent to the user. Accordingly, various embodiments may indicate recommended actions to the user through the use of one or more action indicators, such as action indicator 4040 of FIG. 4C. In general, an action indicator may include any graphical indication of an action recommended to the user. For example, action indicators may instruct a user to pay a bill, ignore a bill, wait for more information, contact customer support, submit a dispute, and various other actions related to a health service or insurance claim.

As described above, each display described herein may graphically indicate a particular state of a process or series of events. In FIG. 4D, display 400 illustrates an additional state that may be indicated by the displays of various embodiments. Visual element 4045 may indicate that the patient's insurance provider has processed the health insurance claim sent by the health services provider. In some cases, other outcomes may be indicated, such as claim denial or claim adjudication.

In many cases, the successful processing of a claim may result in various events, such as the insurance provider sending a payment to the health services provider and/or sending an EOB statement to the patient to which health services were rendered. Such events are illustrated by visual elements 4050 and visual elements 4065 of FIG. 4E. Visual element 4050 includes an indication of an asset and source and destination entities as indicated by EOB icon 4055 and arrow 4060 respectively. Similar to the other arrows of display 400, the tail of arrow 4060 indicates the source entity (e.g., the insurance provider), and the head of arrow 4060 indicates the destination entity (e.g., the patient). In addition to an EOB statement, an insurance provider may transmit a payment to the health services provider for the particular health service rendered. Visual element 4065 illustrates an indication of an asset, such as payment icon 4070, an indication of a source entity (e.g., the insurance provider), such as the tail of arrow 4075, and an indication of a destination entity (e.g., the health services provider), such as the head of arrow 4075.

Figure 4A:
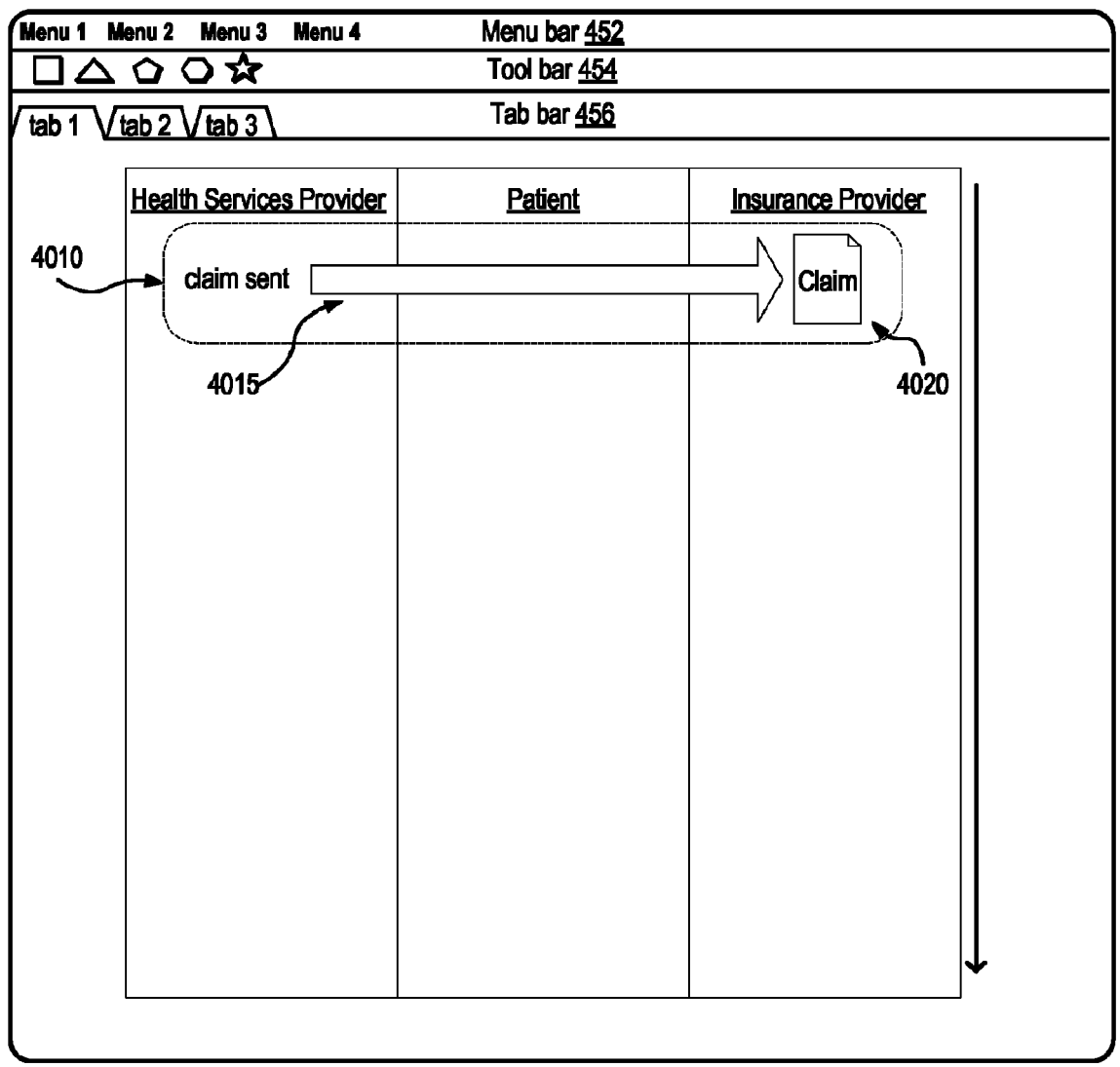
FIGS. 4A-4M illustrate various exemplary displays for indicating the state of a series of events.
Figure 4B:
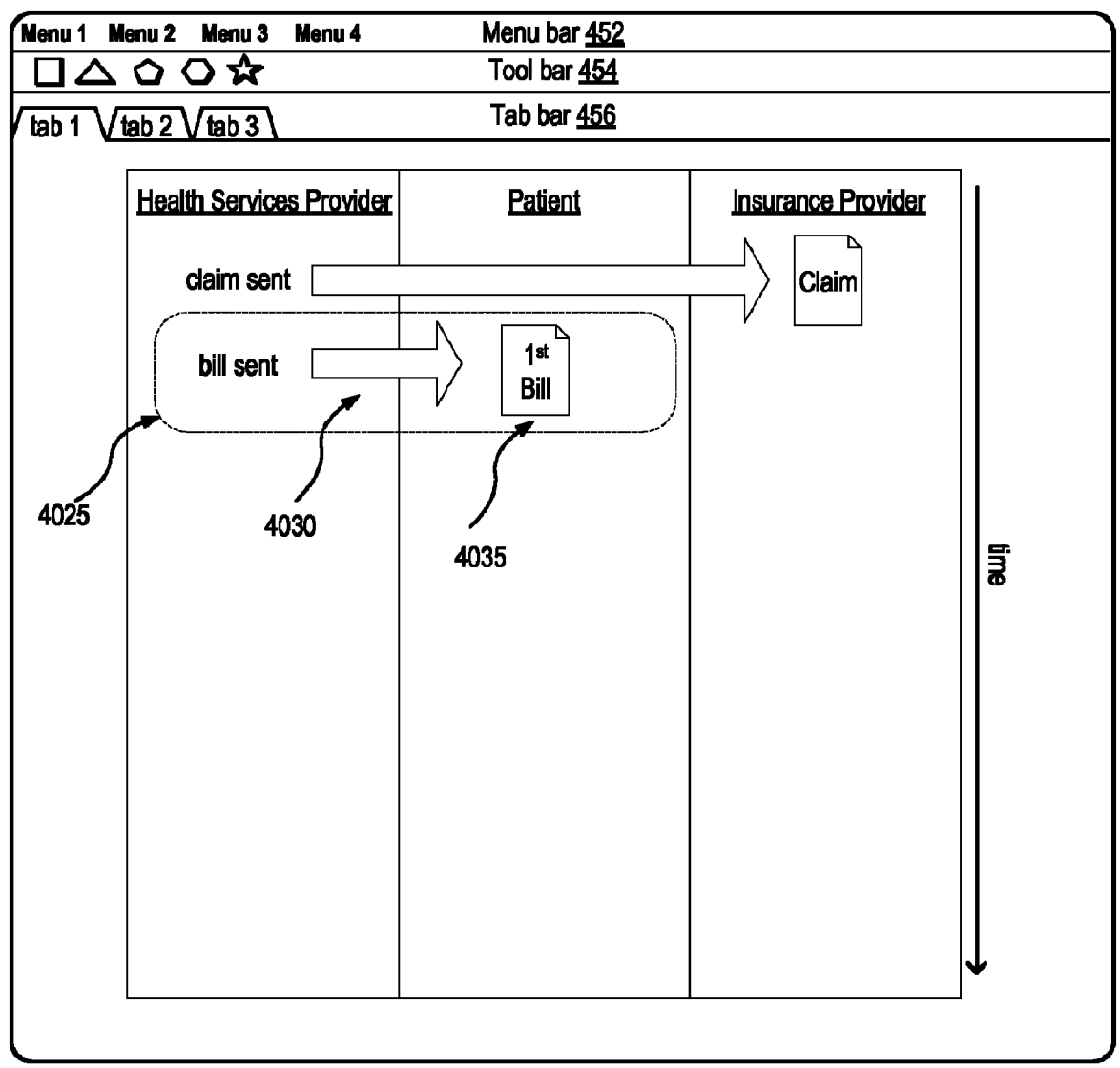
Figure 4C:
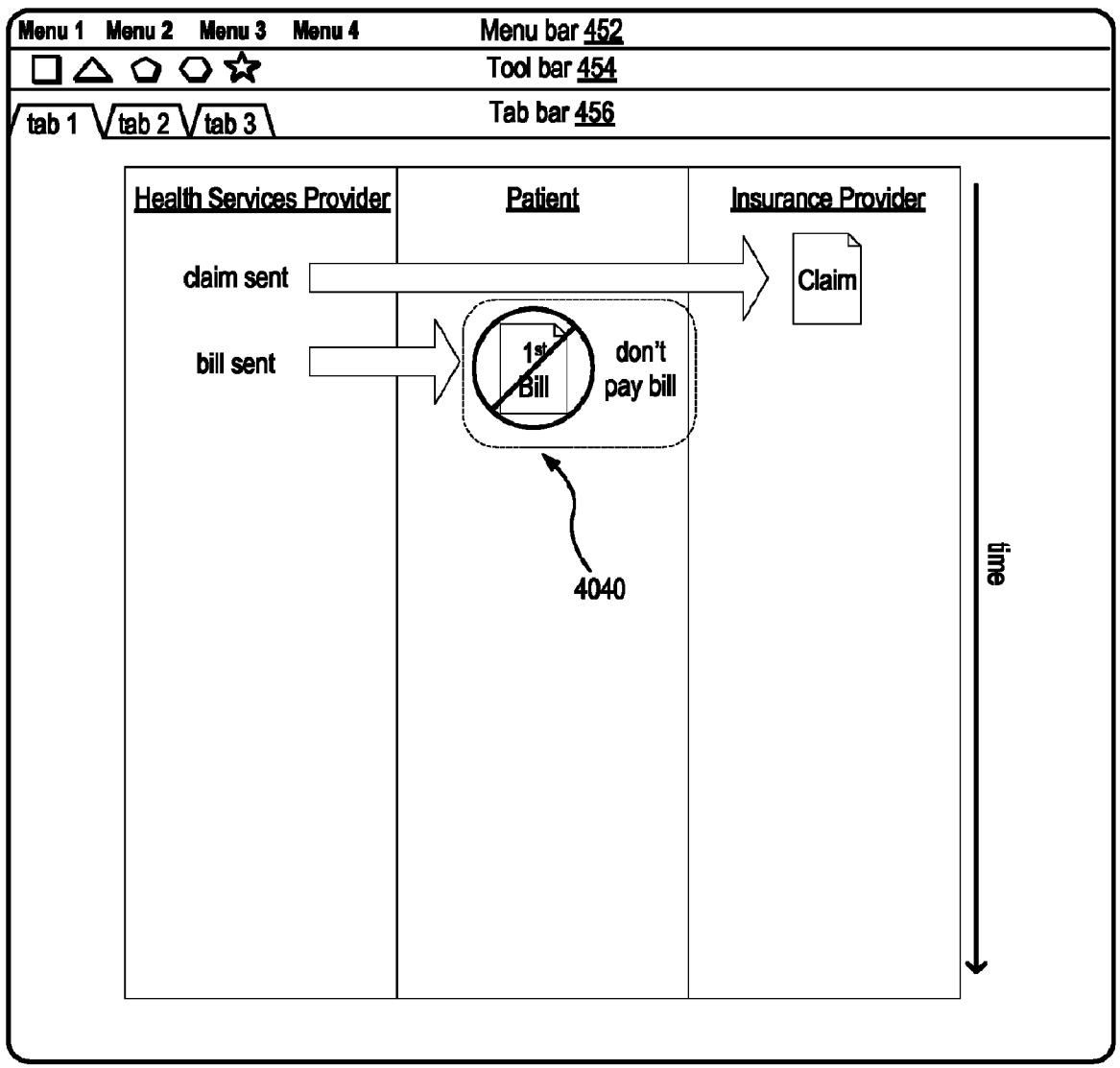
Figure 4D:
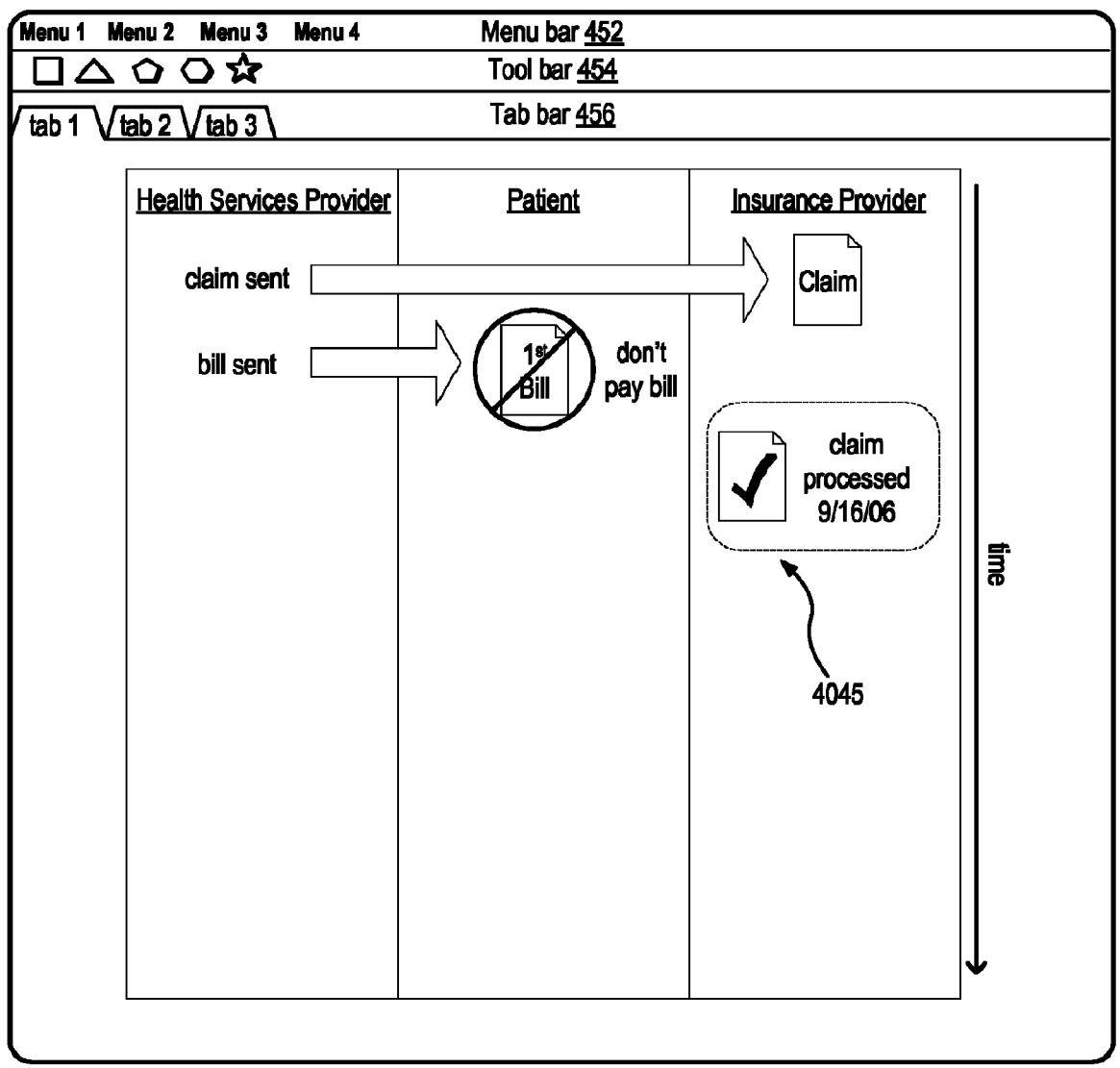
Figure 4E:
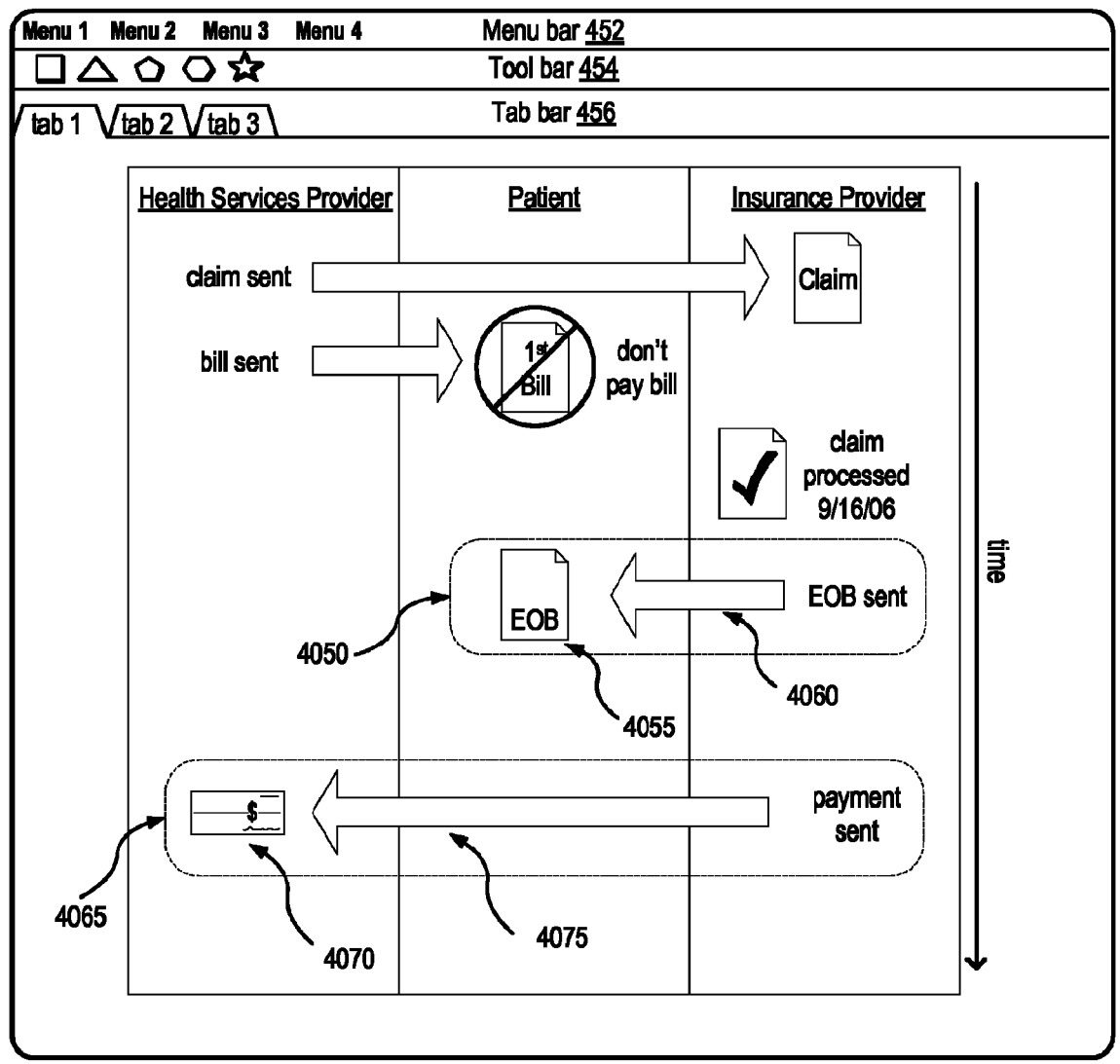
Figure 4F:
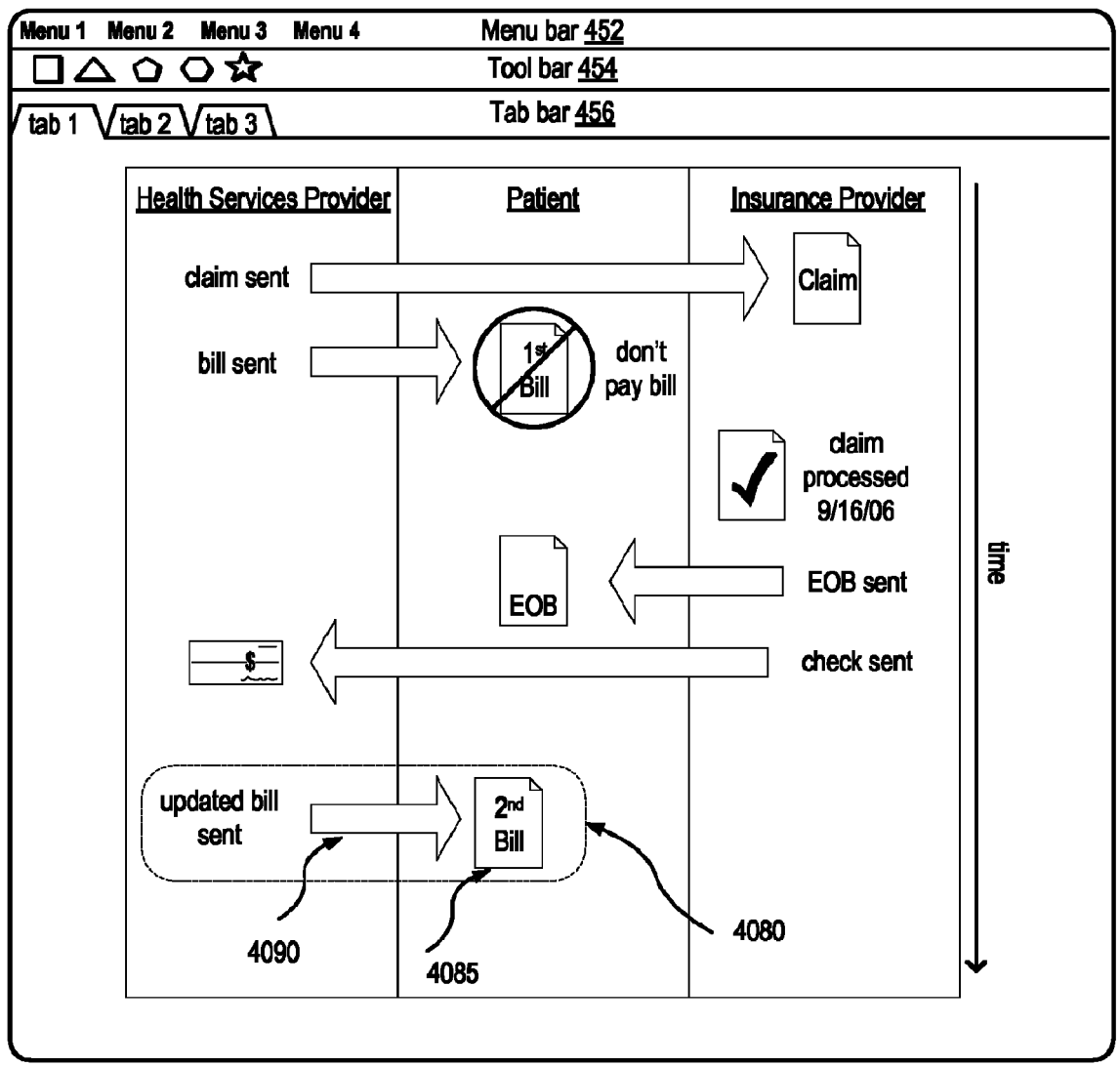
Figure 4G:
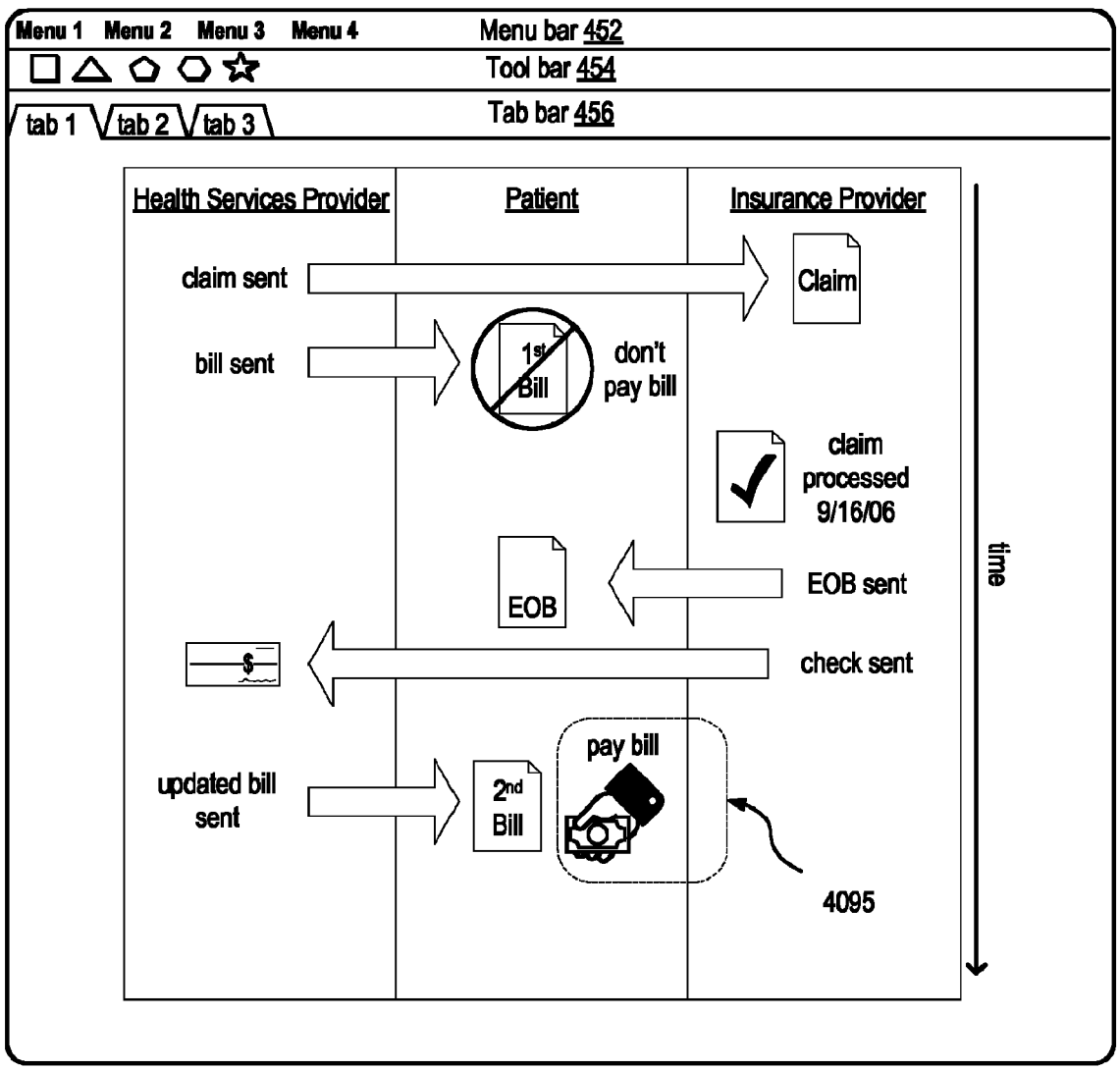
Figure 4H:
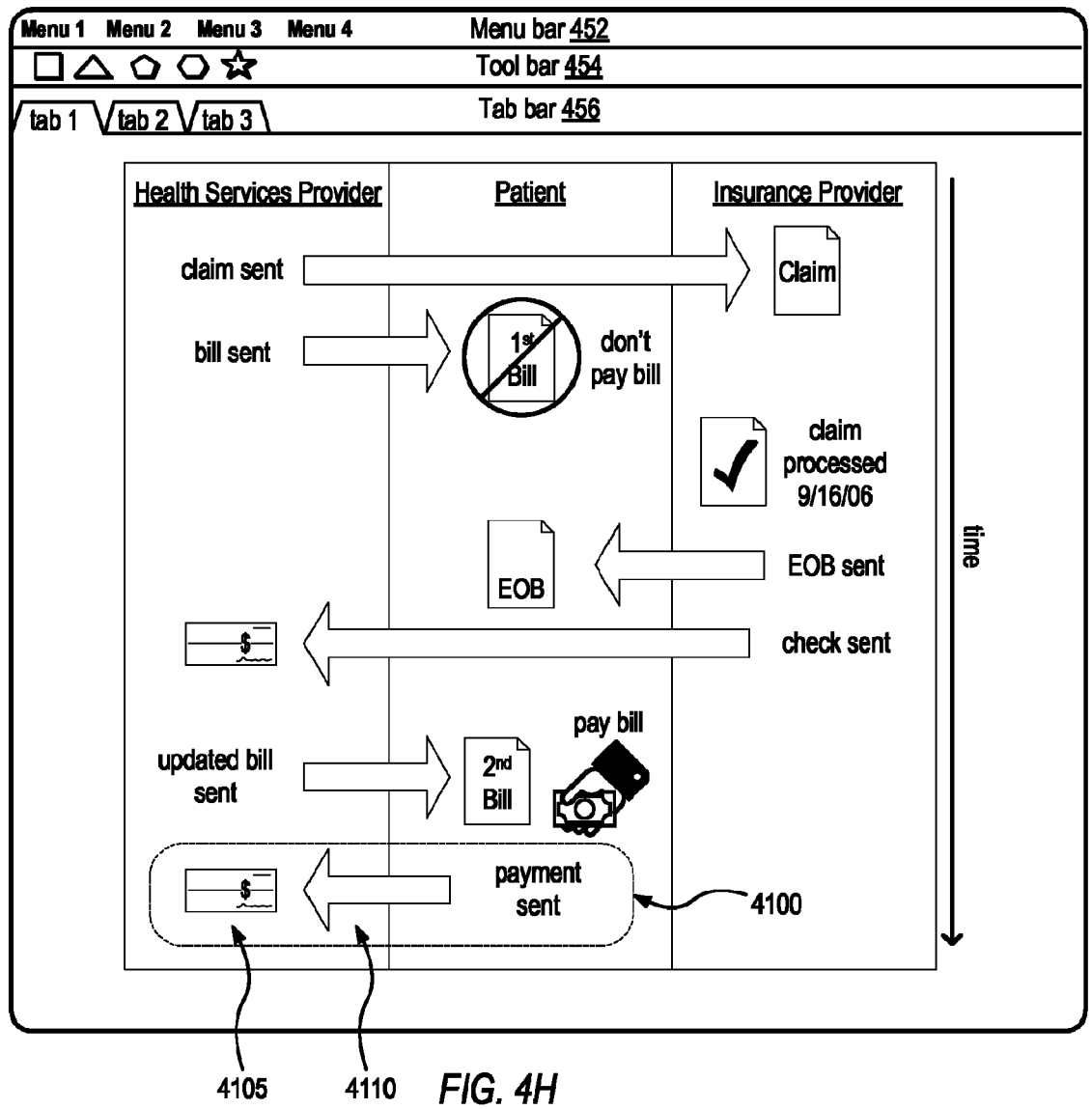

In response to receiving payment from the insurance provider, the health services provider may send an updated bill to the patient as illustrated by visual element 4080 of FIG. 4F. Visual element 4080 includes an indication of an asset (e.g., the $2^{nd}$ bill), such as asset $2^{nd}$ bill icon 4085, an indication of a source entity (e.g., the health services provider), as indicated by the tail of arrow 4090, and an indication of a destination entity (e.g., the patient), as indicated by the head of arrow 4090. Similar to the first bill, display 400 may provide an action indication that indicates an appropriate action to take in response to the bill. As illustrated in FIG. 4G, visual element 4095 provides such an action indication to the user. In other words, visual element 4095 indicates that the patient should provide a payment to the health services provider in response to the $2^{nd}$ bill. Accordingly, the patient may send payment to the health services provider as illustrated by visual element 4100 of FIG. 4H. Visual element 4100 includes an indication of an asset (e.g., the payment), such as asset payment icon 4105, an indication of a source entity (e.g., the patient), as indicated by the tail of arrow 4110, and an indication of a destination entity (e.g., the health services provider), as indicated by the head of arrow 4110.

Figure 4I:
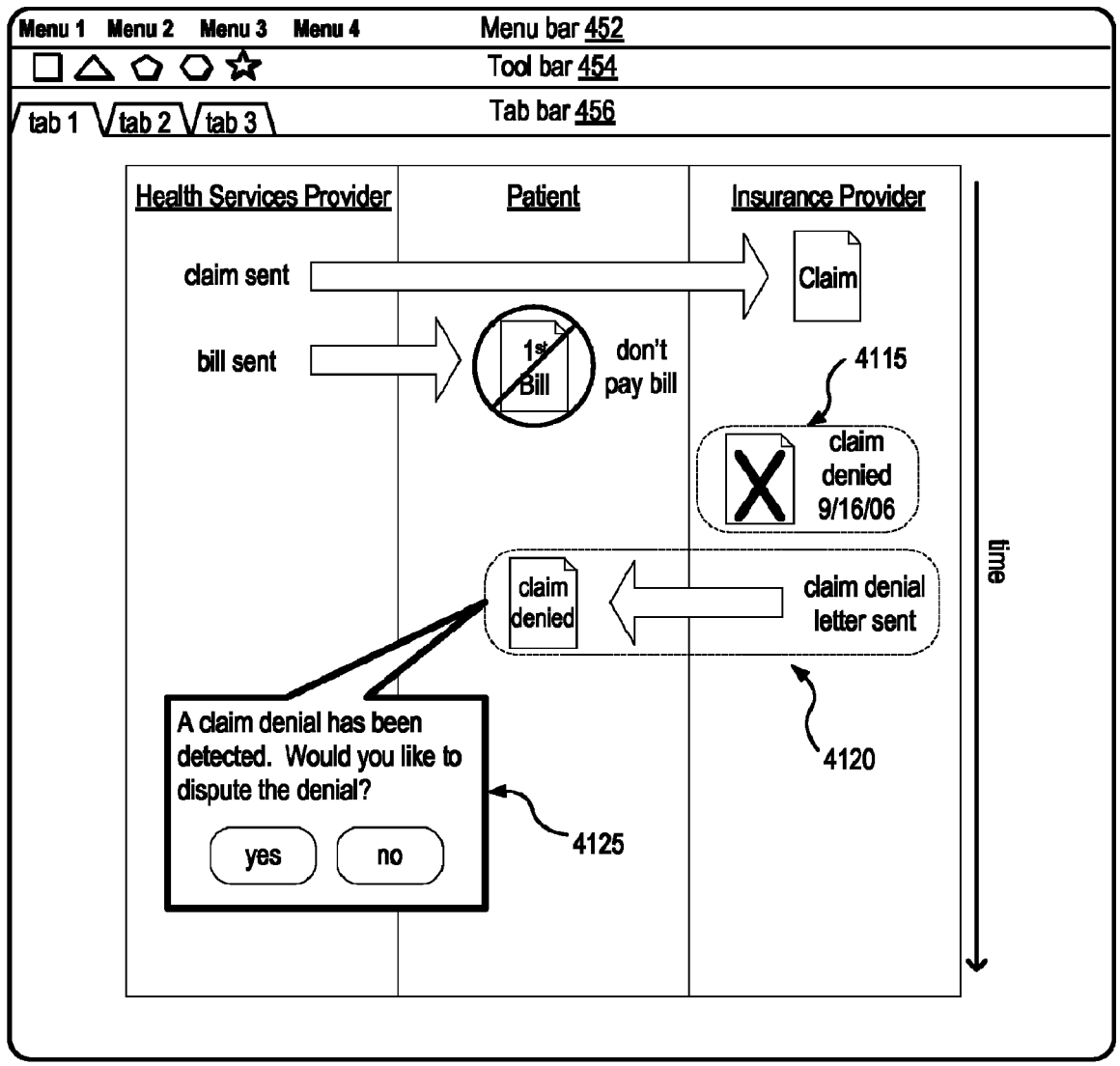

While the above series of displays illustrates an exemplary process associated with the payment of a particular medical service, various embodiments may include other types of displays. In some embodiments, displays defined by data generated by the display generator described herein may include one or more indications of a dispute. Such disputes may include disputes between an individual (e.g., an insured individual or patient) and one more other entities, such as health insurance providers or health services providers. For example, disputes may arise from a health insurance provider denying a claim of an insured individual. For instance, the individual may believe the health insurance company wrongly denied a claim for a procedure that is designated as covered according to the individual's health plan. Another example of a dispute may include a dispute arising from a healthcare provider assessing an improper service charge. For example, if an individual is assessed a charge by a healthcare provider for a medical procedure that was not performed, the individual may seek to dispute the charge. FIG. 4I illustrates a display that includes an indication of a claim denial, such as visual element 4115. In many cases, when an insurance provider denies a patient's claim, the insurance provider may inform the patient by letter (or other correspondence) as illustrated by visual element 4120. Various embodiments may also enable the user (e.g., the patient) to automatically dispute claims. For example, dispute dialog 4125 may prompt a user to dispute one or more denied claims. If the user decides to dispute a claim (e.g., by selecting yes), the display may initiate a dispute resolution process. In some embodiments, various representations (e.g., hardcopy versions, electronic versions, fax versions) of display 400 may be presented to an entity in order to facilitate the resolution of a dispute.

Figure 4J:
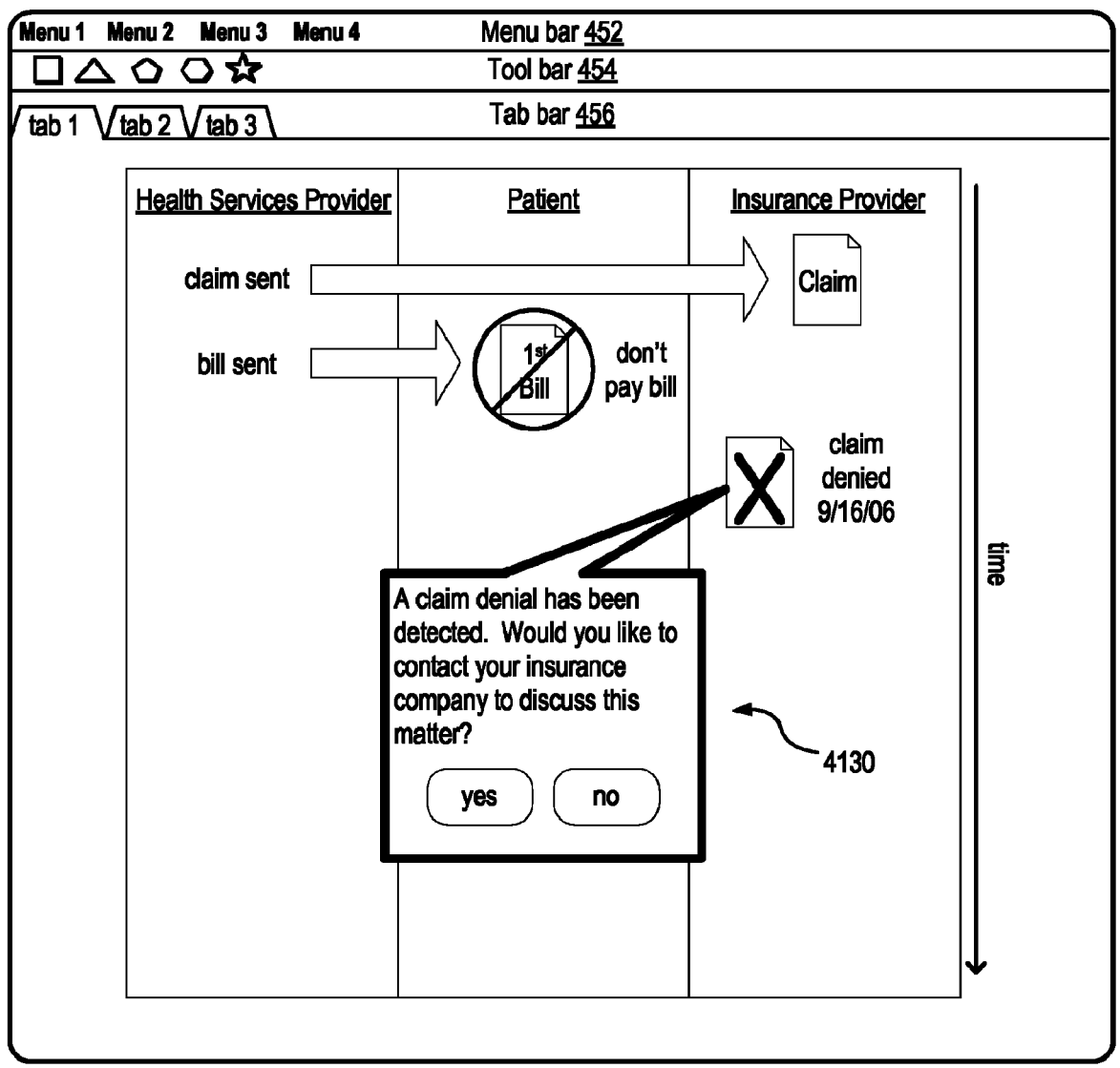

In various embodiments, a dialog display, such as dialog display 4130 of FIG. 4J, may enable a user to contact an entity in the event of a dispute. For example, after choosing to contact the insurance provider through dialog display 4130, the user may be presented with various other displays such as chat or messaging displays for contacting a CSR of the insurance provider. In other cases, display 400 may interface with a voice system (e.g., such as a Voice Over Internet Protocol system) such that the user of the display may communicate to a CSR of the insurance provider. In other cases, an email client may be launched in order to contact a CSR of the insurance provider. Similar functionality may be employed for other entities, such as the health service provider.

Figure 4K:
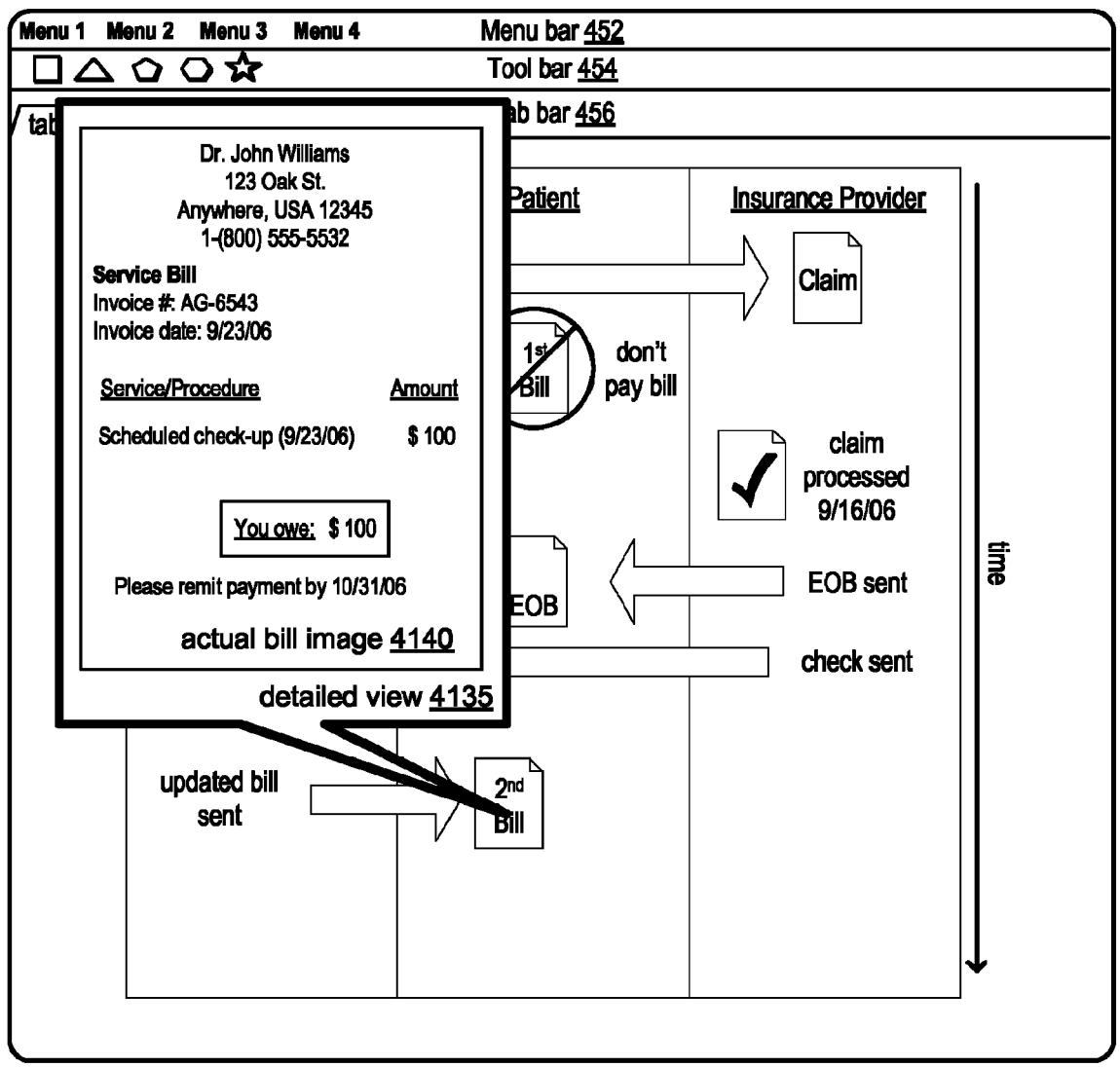

In various embodiments, various elements of display 400 may be viewed in more detail. In some cases, a user may select an element of display 400, such as an indication of an asset (e.g., a bill or invoice icon, a payment icon, a claim icon), and one or more additional displays (also generated by display generator 100 and defined by display data 125) may be presented in response to the user's selection. The additional displays may include an image of the actual asset. For example, if the user selects a payment icon, the additional display may include an image of a payment, such as a check or credit card receipt. Similarly if the user selects an EOB icon, the additional display may include an image an actual EOB statement. FIG. 4K illustrates one example of a detailed view display, such as detailed view display 4135, and an exemplary image of a bill, such as actual bill image 4140. For instance, a user may select $2^{nd}$ bill icon 4085 in order to view an image of the actual bill, such as actual bill image 4140. In various other embodiments, other detailed views may be employed to display images (or other representations) of other types of assets, such as other bills, payments, claims, EOB statements, and other items.

Figure 4L:
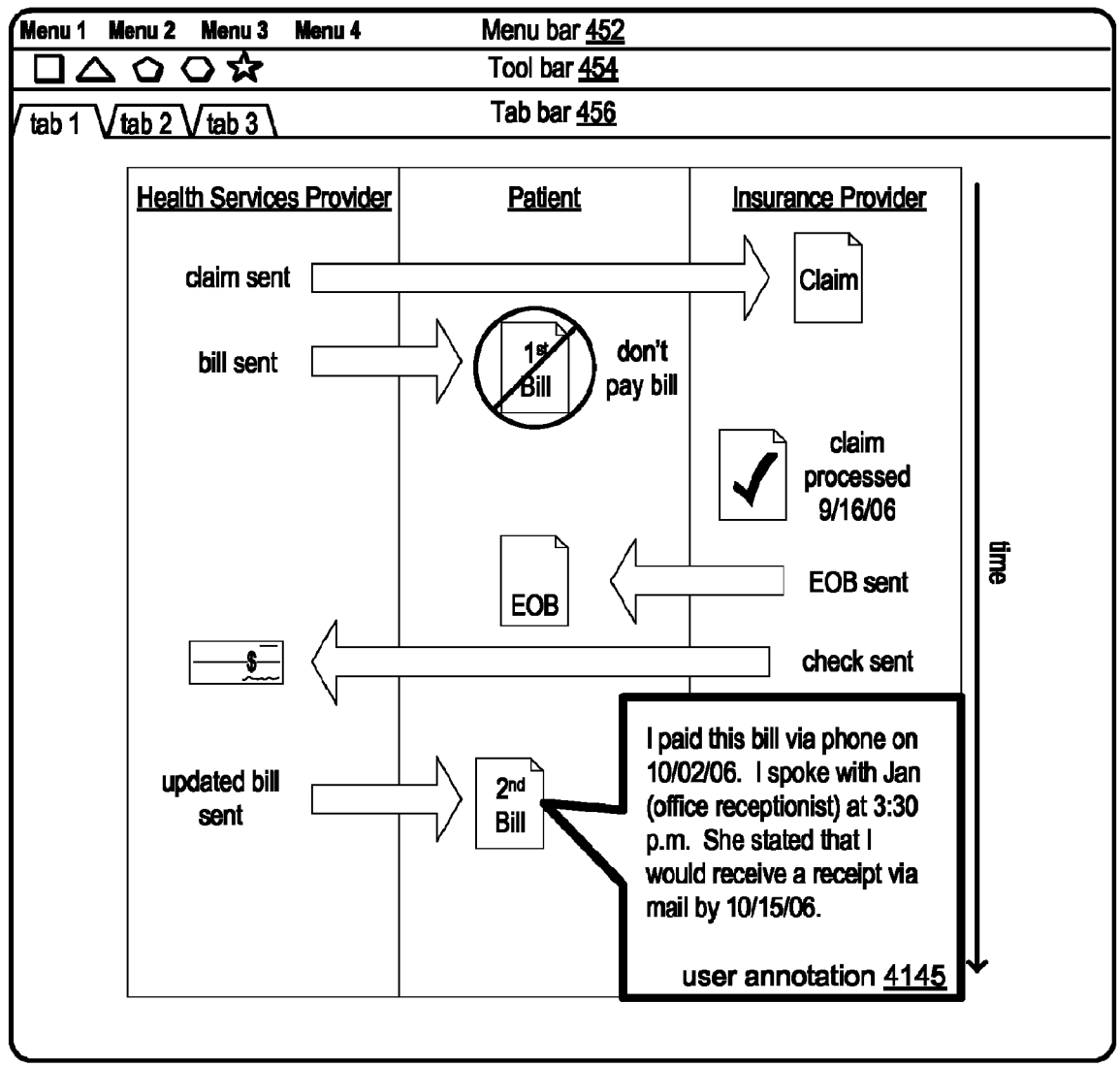

In various embodiments, display 400 may enable a user to add one or more user annotations to the various elements of the display. FIG. 4L illustrates an exemplary user annotation, such as user annotation 4145. The use of user annotations may enable the user to maintain accurate and thorough records of events related to a health service and/or health insurance claim. In the illustrated embodiment, user annotation 4145 may have been created by a user after a telephone conversation with a representative of the health services provider. User annotations may be appended to any portion of display 400. In this manner, the user may append comments, notes, and even additional objects (e.g., files, images, documents), to portions of display 400.

Figure 4M:
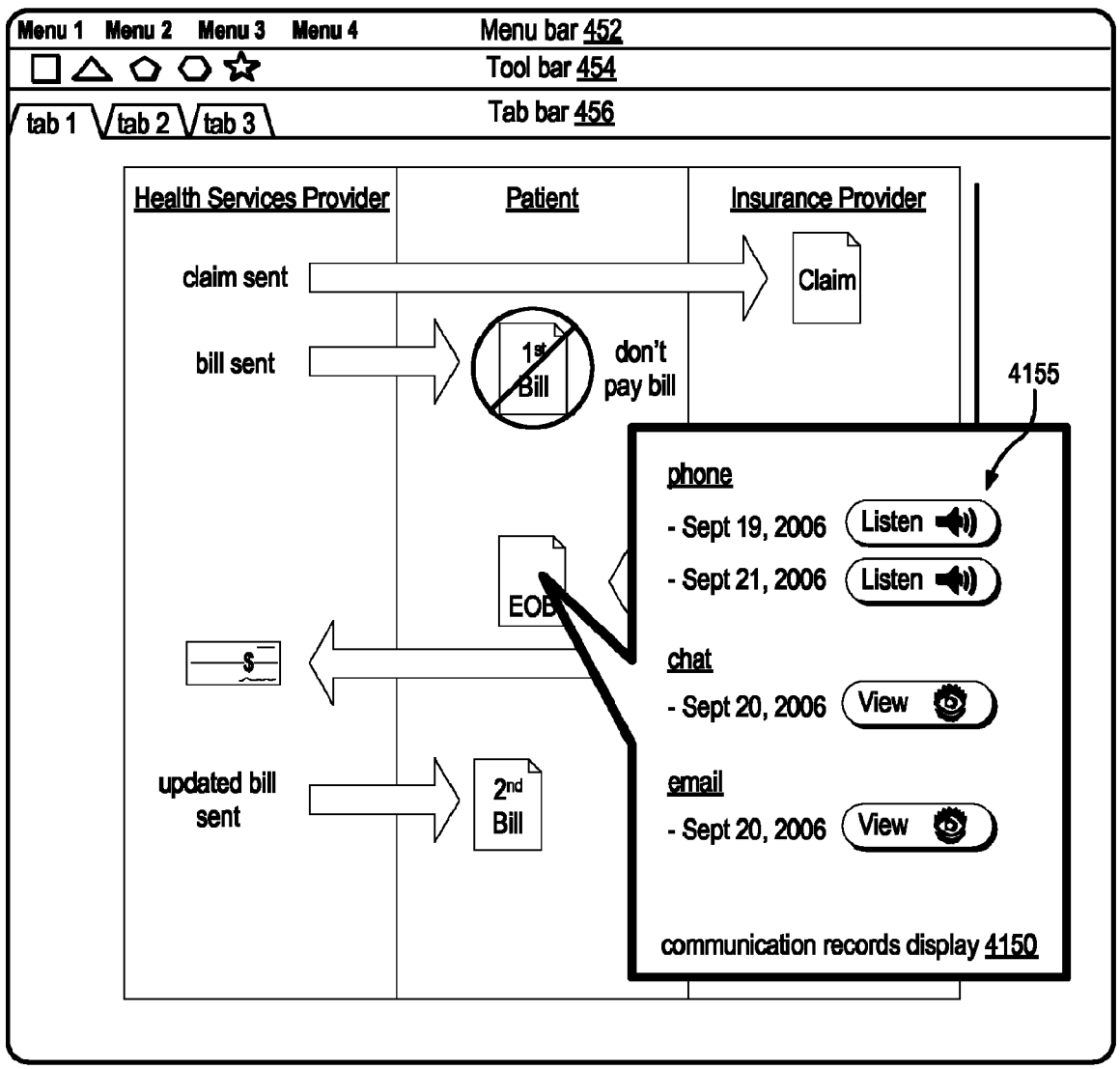

In various embodiments, display 400 may include a display component that enables a user to view one or more communication records associated with an element of display 400. FIG. 4M illustrates an exemplary display component, such as communication records display 4150, that enable a user to access various communication records through one or more controls, such as control 4155. For example, in order to listen to a phone conversation with an insurance company regarding an EOB statement, the user may select control 4155, and the display may effect or initiate the playback of the appropriate conversation. The user may select similar controls for other communication records (e.g., records related to email, chat, and other communications) and the display may effect or initiate the viewing or playback of those records, as well.

The displays described herein may also include various other types of visual elements such as visual elements associated with a dispute (e.g., an indication of a dispute notification, dispute status, or dispute resolution), claim adjudication (e.g., claim adjudication status and/or resolution), and other types of visual elements that do not necessarily include an indication of an asset, source entity, and/or destination entity.

The various displays described herein, such as the displays of FIGS. 4A-N may be defined by data generated by the display generator described herein. In some cases, the display data may be generated for a particular client system, such as a client system associated with an insured individual. In other cases, the display generator may create and/or manage display data for multiple client systems. One example of such an implementation is illustrated by the dataflow diagram of FIG. 5. FIG. 5 illustrates display generator 100 implemented within server 110 and configured to provide display data to multiple clients, such as insurance provider system 250, health services provider system 260, and insured individual system 510. Insurance provider system 250 and health services provider system 260 are described above in regard to FIG. 2. Insured individual system 510 may be a computer system of an insured individual (e.g., a desktop or home computer). Each of the clients may be configured in the manner described above in regard to client 120 of FIG. 1. In other words, each client may access display generator 100 to access client display data in order to view various displays, such as the displays described herein. In most cases, the display data, such as display data 125A-C, may be related. For example, the display data may be related by individual, health service, insurance claim, episode, and other health related items. Accordingly, an insured individual, health services provider, and an insurance provider may each view related displays, such as the various displays described herein. This functionality may facilitate the resolution of disputes and any other situation where it is important that multiple parties are viewing the same information.

In some cases, each portion of related data (e.g., display data 125A-C) may be the same data. In other words, each entity may receive the same data and view the same displays defined by that data. However, in some cases, the related data may be similar while not necessarily the same. For example, display data 125A-C may be similar yet each portion of display data may include some differences, such as personal settings, user-supplied data, and other data that differs among entities. For instance, each portion of display data may contain the same data in regard to data that defines events associated with a health service (e.g., the data described above in regard to the various visual elements of display 400) and different data in regard to data that defines user annotations (e.g., user annotation 4145), communication records (e.g., communication records display 4150), and data that a user would like to keep private.

In some embodiments, each user (e.g., an insured individual, insurance provider, health services provider) may utilize their respective system to customize their displays and provide the data that defines such customizations to display generator 100. In response, display generator 100 may update the respective portion of display data to reflect the user customizations. For example, in some embodiments, a user may manually add elements, such as visual elements, to a display. For instance, a user may have paid a particular bill by sending a payment to a health services provider. If an error occurs and display generator does not receive an indication of such a payment (e.g., if the health services provider does not send the display generator data that indicates such a payments was received), the payment may not be reflected in the display data sent to the various entities (e.g., display data 125A-C). Accordingly, in this example, it may be desirable for the user to manually add elements, such as the visual elements described above, to a display defined by their respective display data. In various embodiments, display generator 100 may capture the data that defines such an element and update the respective data accordingly. For example, an insured individual may use insured individual system 510 to add a visual element (e.g., a visual element associated with a payment) to a display defined by display data 125C. For instance, the user could "drag-and-drop" visual elements onto the display in order to create a visual element. Display generator 100 may detect the new visual element and associated data and add that data to display data 125C. In this manner, display generator 100 may update display data 125C with data added from the user; accordingly, displays defined by such data may be updated as well. In some cases, this data may also include data associated with user annotations, communication records, and any other element described above in regard to FIG. 4. In some cases, updates made to one portion of display data may also be made to other portions data. In this way, changes made by one entity may be viewed by all entities.

In some embodiments, each portion of display data may include shared data (i.e., accessible to other entities) and private data (i.e., inaccessible to other entities). For instance, in one embodiment, data that defines visual elements of a display data may be categorized as shared data whereas data associated with user annotations may be categorized as private data. For instance, the user may have extensive user annotations saved within their respective display data; however, the user's annotations may contain private information that the user does not desire to share with other entities. In this manner, various embodiments may enable a user to view a shared display or a private display. For instance, a shared display may be defined by data that is accessible to all entities whereas a private display may be defined by data that is inaccessible to entities other than the user.

Figure 6:
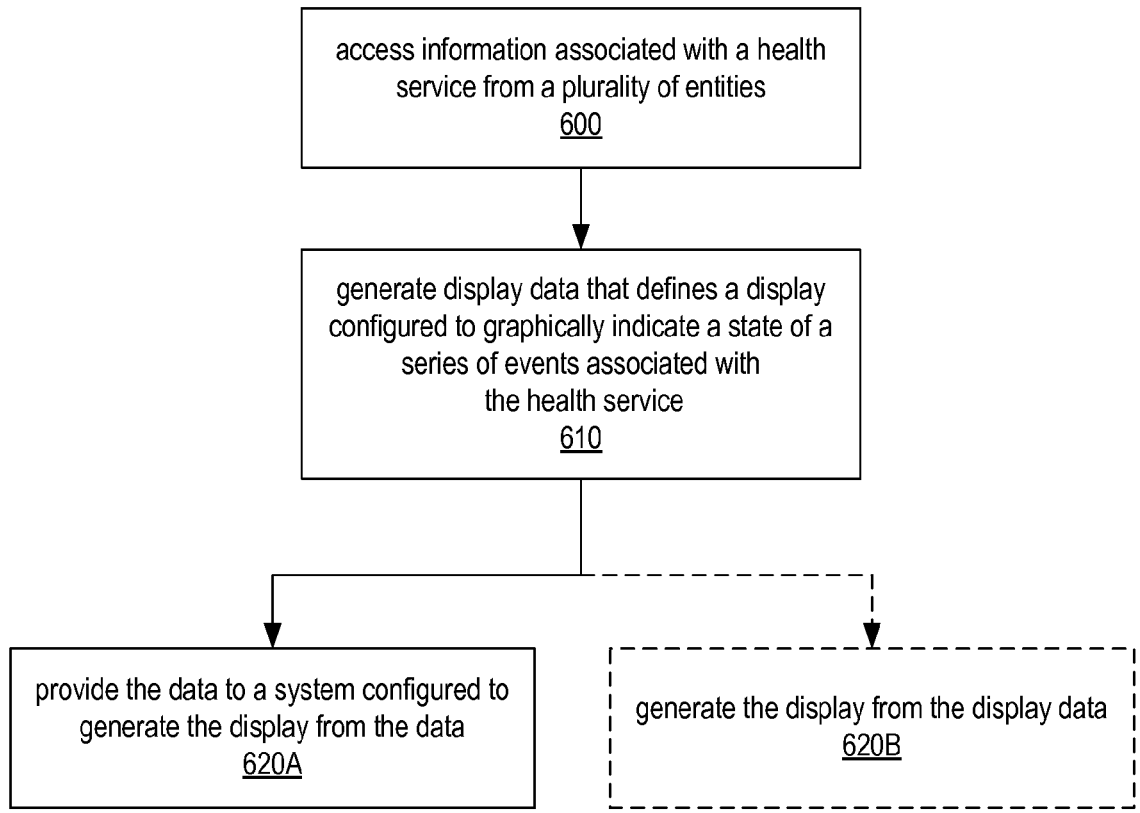
FIG. 6 illustrates an exemplary method for generating display data, as described herein.

Various methods may be employed to create the displays described herein, such as the displays of FIGS. 4A-N. An exemplary method for creating such displays is illustrated by the flowchart of FIG. 6. As illustrated by block 600, the method may include accessing information associated with a health service from a plurality of entities. Such entities may include health services providers, insurance providers, and other entities such as insured individuals. In some cases, the method may include accessing information from computer systems associated with the entities. For instance, in one embodiment, an entity may provide a web service that services requests for data associated with a health service. In such an embodiment, the method may include requesting and receiving data from the web service. In other cases, the entities may provide one or more databases that may be queried for data associated with one or more health services. In general, any method of accessing data may be employed to access data associated with a health service from the various entities.

In various embodiments, the method may include accessing various types of data associated with a health service. For instance, the method may include accessing data that relates to the status of a health insurance claim from a health insurance provider. For example, the data accessed may indicate that a health insurance claim for a health service is currently undergoing adjudication. In other cases, the data accessed may indicate that the health insurance claim has been processed, denied, or disputed. In general, the method may include accessing any status information associated with the processing of a health insurance claim. In another example, the method may include accessing data that relates to the status of health insurance claim from a health services provider (e.g., a physicians office, hospital, and/or their associated computer systems). The method may also include accessing other information such as the status of bill payments for health service bills (or invoices) from a health services provider. For instance, the health services provider may indicate that a bill has been sent, that a payment has been received, or that a dispute over the payment has occurred. The method may also include accessing data (e.g., from a database or other data source or from a user) from an individual, such as an insured individual. For example, an insured individual may indicate to the display generator described herein that the individual has paid a particular bill or invoice. The method may also include accessing data that indicates various events including, but not limited to, the health services provider sending an insurance claim (on behalf of the insured individual) to the insurance company, the health services provider sending a bill to the insured individual, the insurance company processing the insurance claim, the insurance company sending an Explanation of Benefits (EOB) statement to the insured individual, the insurance company providing a payment to the health services provider, and/or the insured individual providing a payment to the health services provider. Additionally, the method may include accessing any data that defines a display or visual element of a display, such as the displays and visual elements described above in regard to FIG. 4.

The method may also include accessing data that includes an indication of an asset, a source entity, and a destination entity. In various embodiments, the displays defined by the display data may include one or more visual elements. The visual elements may graphically indicate an event that includes the transfer of an asset (e.g., data, information, or payments) between a source entity (i.e., the entity providing the asset) and a destination entity (i.e., the entity receiving the asset). For example, an exemplary event may include an individual (the source entity in this example) providing a health services provider (the destination entity in this example) with a payment (the asset in this example). The displays and/or display data generated by the display generator may include multiple visual elements in order to graphically indicate the current state of a process, such as processes associated with health services or payments for such health services.

As illustrated by block 610, the method may also include generating display data that defines a display configured to graphically indicate a state of a series of events associated with a healthcare related service. For example, during the processing of a health insurance claim, numerous events typically take place, such as the sending or filing of the claim, processing of payments, claim adjudication, and other claim related events. The display may include multiple chronologically ordered visual elements each associated with one of said portions of information. For example, one visual element may indicate the filing of an insurance claim whereas another may indicate subsequent adjudication of the claim. In some cases, the method may include generating the display data such that the visual elements defined by the display data indicate an asset associated with a healthcare-related service, a source entity that provided the asset (e.g., an individual or patient, health services provider, or an insurance company), and/or a destination entity that received the asset from the source entity (e.g., an individual or patient, health services provider, or an insurance company). In this way, the display data created by the method described herein may utilize one or more visual elements to indicate the state of a series of events related to a health service to a user of the display.

In some cases, as illustrated by block 620A, the method may include providing the display data to a system configured to generate the display defined by the display data. For example, in one embodiment, the method described herein may be implemented by a server, such as server 110, and include providing display data to a client, such as client 120. In some cases, the method may include providing the display data to multiple clients, such as via the Internet. In some embodiments, the method may include providing a web service, database, or other data distribution tool such that multiple clients may access the display data over a network. For instance, in some embodiments, a client configured to run a healthcare management application may access the display data from a server configured to implement the method described herein. For example, the healthcare management application may initiate a service call or request to a web service for the display data. In other embodiments, the method may include generating the display from the display data as illustrated by block 620B. For example, the method described herein may be implemented by a stand-alone computer system configured to run a healthcare management application. In such an embodiment, the healthcare management application may both generate the display data and generate the display defined by the display data (e.g., presenting the display to the user through a computer monitor).

In some cases, the system and method for generating a display may be applied to a variety of other types of entities other than health services provider, individuals/patients, and/or health insurance providers. Similarly, the system and method for generating a display may be applied to numerous types of assets related to items other than assets associated with a health service. For example, in one embodiment, the system and method described herein may be applied to a series of events associated with an automobile, home, or other insurance claims. For instance, display data of such a system might graphically indicate a state of events associated with a car accident. This example might include the transfer of an asset (e.g., claims filings, payments, information, and other items) between one or more source and destination entities including, but not limited to, the automobile owner, the automobile insurance company, and a repair shop. In other cases, the system and method for generating a display may be applied a series of events associated with the purchase of a home. Such an embodiment might include one or more assets (e.g., credit application filings, proof of income, credit reports, payments, and other information) and multiple source and destination entities including, but not limited to, a homebuyer, homeowner, bank or lender, and/or a real estate company. One of ordinary skill in the art will readily recognize how various other embodiments may be applied to other series' of events, assets, and source and destination entities.

Exemplary System

Various embodiments of a system and method for generating a display configured to graphically indicate a state of a series of events, as described herein, may be executed on one or more computer systems, which may interact with various other devices. One such computer system is computer system 700 illustrated by FIG. 7. Computer system 700 may be capable of implementing a display generator as illustrated by display generator 100. Computer system 700 may also be capable of storing display data, such as display data 125. In the illustrated embodiment, computer system 700 includes one or more processors 710 coupled to a system memory 720 via an input/output (I/O) interface 730. Computer system 700 further includes a network interface 740 coupled to I/O interface 730, and one or more input/output devices 750, such as cursor control device 760, keyboard 770, and display(s) 780. In some embodiments, it is contemplated that embodiments may be implemented using a single instance of computer system 700, while in other embodiments multiple such systems, or multiple nodes making up computer system 700, may be configured to host different portions or instances of embodiments. For example, in one embodiment some elements may be implemented via one or more nodes of computer system 700 that are distinct from those nodes implementing other elements.

In various embodiments, computer system 700 may be a uniprocessor system including one processor 710, or a multiprocessor system including several processors 710 (e.g., two, four, eight, or another suitable number). Processors 710 may be any suitable processor capable of executing instructions. For example, in various embodiments processors 710 may be general-purpose or embedded processors implementing any of a variety of instruction set architectures (ISAs), such as the x86, PowerPC, SPARC, or MIPS ISAs, or any other suitable ISA. In multiprocessor systems, each of processors 710 may commonly, but not necessarily, implement the same ISA.

System memory 720 may be configured to store program instructions 722 and/or data 732 accessible by processor 710. In various embodiments, system memory 720 may be implemented using any suitable memory technology, such as static random access memory (SRAM), synchronous dynamic RAM (SDRAM), nonvolatile/Flash-type memory, or any other type of memory. In the illustrated embodiment, program instructions and data implementing a display generator, such as display generator 100 described above, are shown stored within system memory 720 as display generator 100. In other embodiments, program instructions and/or data may be received, sent or stored upon different types of computer-accessible media or on similar media separate from system memory 720 or computer system 700. Generally speaking, a computer-accessible medium may include storage media or memory media such as magnetic or optical media, e.g., disk or CD/DVD-ROM coupled to computer system 700 via I/O interface 730. Program instructions and data stored via a computer-accessible medium may be transmitted by transmission media or signals such as electrical, electromagnetic, or digital signals, which may be conveyed via a communication medium such as a network and/or a wireless link, such as may be implemented via network interface 740.

In one embodiment, I/O interface 730 may be configured to coordinate I/O traffic between processor 710, system memory 720, and any peripheral devices in the device, including network interface 740 or other peripheral interfaces, such as input/output devices 750. In some embodiments, I/O interface 730 may perform any necessary protocol, timing or other data transformations to convert data signals from one component (e.g., system memory 720) into a format suitable for use by another component (e.g., processor 710). In some embodiments, I/O interface 730 may include support for devices attached through various types of peripheral buses, such as a variant of the Peripheral Component Interconnect (PCI) bus standard or the Universal Serial Bus (USB) standard, for example. In some embodiments, the function of I/O interface 730 may be split into two or more separate components, such as a north bridge and a south bridge, for example. Also, in some embodiments some or all of the functionality of I/O interface 730, such as an interface to system memory 720, may be incorporated directly into processor 710.

Network interface 740 may be configured to allow data (e.g., display data 125) to be exchanged between computer system 700 and other devices attached to a network (e.g., network 180), such as other computer systems (e.g., client 120), or between nodes of computer system 700. In various embodiments, network interface 740 may support communication via wired or wireless general data networks, such as any suitable type of Ethernet network, for example; via telecommunications/telephony networks such as analog voice networks or digital fiber communications networks; via storage area networks such as Fibre Channel SANs, or via any other suitable type of network and/or protocol.

Input/output devices 750 may, in some embodiments, include one or more display terminals, keyboards, keypads, touchpads, scanning devices, voice or optical recognition devices, or any other devices suitable for entering or accessing data by one or more computer system 700. Multiple input/output devices 750 may be present in computer system 700 or may be distributed on various nodes of computer system 700. In some embodiments, similar input/output devices may be separate from computer system 700 and may interact with one or more nodes of computer system 700 through a wired or wireless connection, such as over network interface 740.

Figure 7:
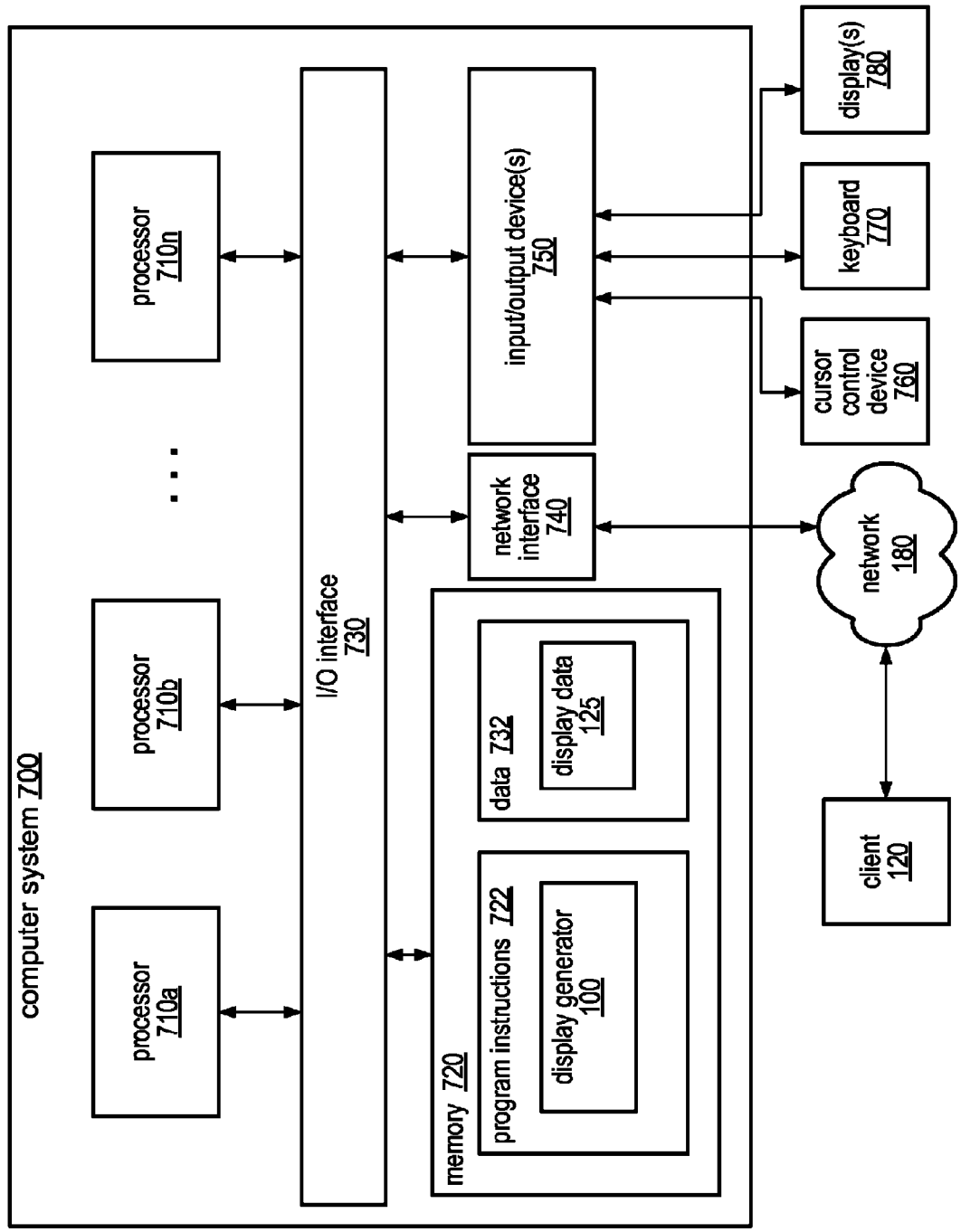
FIG. 7 illustrates a computing system suitable for implementing a display generator, according to one embodiment.

As shown in FIG. 7, memory 720 may include program instructions 722 configured to implement a display generator, such as display generator 100. Memory 720 may also include data 732 including various display data, such as display data 125.

In one embodiment, display generator 100 may be configured to implement the method described in FIG. 6. In other embodiments, different elements and data may be included.

Those skilled in the art will appreciate that computer system 700 is merely illustrative and is not intended to limit the scope of the present invention. In particular, the computer system and devices may include any combination of hardware or software that can perform the indicated functions, including computers, network devices, Internet appliances, PDAs, wireless phones, pagers, etc. Computer system 700 may also be connected to other devices that are not illustrated, or instead may operate as a stand-alone system. In addition, the functionality provided by the illustrated components may in some embodiments be combined in fewer components or distributed in additional components. Similarly, in some embodiments, the functionality of some of the illustrated components may not be provided and/or other additional functionality may be available.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via intercomputer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 700 may be transmitted to computer system 700 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-accessible medium. Accordingly, the present invention may be practiced with other computer system configurations.

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. SDRAM, DDR, RDRAM, SRAM, etc.), ROM, etc., as well as transmission media or signals such as electrical, electromagnetic, or digital signals, conveyed via a communication medium such as network and/or a wireless link.

The methods may be implemented in software, hardware, or a combination thereof, in different embodiments. In addition, the order of method(s) may be changed, and various elements may be added, reordered, combined, omitted, modified, etc. Various modifications and changes may be made as would be obvious to a person skilled in the art having the benefit of this disclosure.

Realizations in accordance with the present invention have been described in the context of particular embodiments. These embodiments are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the exemplary configurations may be implemented as a combined structure or component. These and other variations, modifications, additions, and improvements may fall within the scope of the invention as defined in the claims that follow.

What is claimed is:

1. A system, comprising:
a processor; and
a memory coupled to the processor, wherein the memory comprises program instructions executable by the processor which when executed by the processor perform a process comprising:
receive, at a personal computing system associated with a consumer user, event information comprising a plurality of events associated with financial aspects of a health related service provided by a health services provider, wherein one or more portions of the event information are provided by each of an insurance provider, the consumer user, and the health services provider; and
generate display data that defines a display configured to graphically indicate a state of each event within the plurality of events, wherein to graphically indicate the state of the series of events the display comprises generating a plurality of chronologically ordered visual elements each associated with the event information, wherein the visual elements graphically indicate:
one or more claims filed by the health services provider with the insurance provider;
one or more payments associated with the health related service, the one or more payments being made either by the consumer user or by the insurance provider to the health service provider; and
one or more action indicators, each action indicator indicating at least one action to be performed in response to the state of one or more events of the plurality of events, each action indicator representing a recommendation provided to the consumer user as to a next action the consumer user is recommended to perform or not perform with respect to payment settlement relating to the health related service, based at least on the event information received.

2. The system of claim 1, wherein one or more of the visual elements are user-selectable, wherein the display is configured to present an image of a document relating to a given event, in response to a user selection of a visual element relating to the event.

3. The system of claim 2, wherein the image is one or more of: an image of an explanation of benefits (EOB) statement, an image of a bill, an image of a payment.

4. The system of claim 1, wherein the instructions are further executable to generate other display data to define another display configured to provide a launch point for said display.

5. The system of claim 4, wherein said launch point comprises a user-selectable health service entry associated with said health related service.

6. The system of claim 1, wherein the program instructions are further configured to generate additional data for one or more additional displays each configured to graphically indicate the state of the series of events associated with said health related service.

7. The system of claim 6, wherein the program instructions are further configured to provide said display data to an entity and provide said additional data to a separate entity, wherein said additional data differs from said display data.

8. The system of claim 1, wherein said display enables a user to make a payment for the health related service.

9. The system of claim 8, wherein said display enables the user to make a single payment for a plurality of health related services associated comprising the health related service and associated with a same episode.

10. The system of claim 1, wherein said action to be performed indicates a bill should be paid.

11. The system of claim 1, wherein said action to be performed indicates a bill should be ignored.

12. The system of claim 1, wherein said display indicates one or more of: a bill, an insurance claim, and/or a payment.

13. The system of claim 1, wherein said display is configured to display one or more user annotations.

14. The system of claim 1, wherein said display enables a user to contact an entity associated with one or more of said visual elements.

15. The system of claim 1, wherein one or more of said visual elements are associated with a dispute.

16. The system of claim 1, wherein one or more portions of said information are provided by an insured individual.

17. A nontransitory computer-readable storage medium, comprising program instructions computer-executable to implement:
receive, at a personal computing system associated with a consumer user, event information comprising a plurality of events associated with financial aspects of a health related service provided by a health services provider, wherein one or more portions of the event information are provided by each of an insurance provider, the consumer user, and the health services provider; and
generate display data that graphically indicates a state of each event within the plurality of events, wherein to graphically indicate the state of the series of events the display comprises generating a plurality of chronologically ordered visual elements each associated with the event information, wherein the visual elements graphically indicate:
one or more claims filed by the health services provider with the insurance provider;
one or more payments associated with the health related service, the one or more payments being made either by the consumer user or by the insurance provider to the health service provider; and
one or more action indicators, each action indicator indicating at least one action to be performed in response to the state of one or more events of the plurality of events, each action indicator representing a recommendation provided to the consumer user as to a next action the consumer user is recommended to perform or not perform with respect to payment settlement relating to the health related service, based at least on the event information received.

18. The medium of claim 17, wherein the one or more visual elements are user-selectable, wherein generating the display data comprises generating the display data to present an image of a document relating to an event associated with the selected visual element in response to a user selection of the associated visual element.

19. The medium of claim 18, wherein the image is one or more of: an image of an explanation of benefits (EOB) statement, an image of a bill, an image of a payment.

20. The medium of claim 17 wherein the program instruction are further configured to generate additional data for one or more additional displays each configured to graphically indicate the state of the series of events associated with said health related service.

21. The medium of claim 20, wherein the program instruction are further configured to provide said display data to an entity and providing said additional data to a separate entity, wherein said additional data differs from said display data.

22. The medium of claim 17, wherein generating the display data comprises generating the display data such that the display is configured to interact with a payment system that enables a user to pay for said service.

23. The medium of claim 22, wherein generating the display data comprises generating the display data such that the user may use the display to make a single payment for a plurality of services comprising said service and associated with a same episode.

24. The medium of claim 17, wherein said action to be performed indicates a bill should be paid.

25. The medium of claim 17, wherein said action to be performed indicates a bill should be ignored.

26. The medium of claim 17, wherein generating the display data comprises generating display data which graphically indicates one or more of: a bill, an insurance claim, and/or a payment.

27. The medium of claim 17, wherein the program instruction are further configured to generate other display data to define another display configured to provide a launch point for said display, wherein said launch point comprises a user-selectable service entry associated with said service.

28. The medium of claim 17, wherein generating the display data comprises generating the display data such that the display data defines one or more user annotations for said display.

29. The medium of claim 17, wherein generating the display data comprises generating the display data such that the display enables a user to contact an entity associated with one or more of said visual elements.

30. The medium of claim 17, wherein one or more of said visual elements are associated with a dispute.

31. The medium of claim 17, wherein one or more portions of said information are accessed from an insured individual.

* * * * *

UNITED STATES PATENT AND TRADEMARK OFFICE
CERTIFICATE OF CORRECTION

| | | |
|---|---|---|
| PATENT NO. | : 7,996,239 B1 | Page 1 of 1 |
| APPLICATION NO. | : 11/829652 | |
| DATED | : August 9, 2011 | |
| INVENTOR(S) | : Suzanne Pellican and Robert Pellican | |

It is certified that error appears in the above-identified patent and that said Letters Patent is hereby corrected as shown below:

On the Title Page, at Item 73, replace "CT" with --CA--;

In Column 19, Line 17, Claim 9, between "services" and "comprising" delete "associated"; and In Column 20, Lines 42-43, Claim 27, replace "instruction" with --instructions--.

Signed and Sealed this

Second Day of October, 2012

David J. Kappos
*Director of the United States Patent and Trademark Office*